United States Patent [19]
White et al.

[11] Patent Number: 6,107,280
[45] Date of Patent: *Aug. 22, 2000

[54] ANTITHROMBOTIC MATERIALS AND METHODS

[75] Inventors: Mark L. White, Sonoma; William Steve Ammons, Pinole, both of Calif.

[73] Assignee: XOMA Corporation, Berkeley, Calif.

[*] Notice: This patent is subject to a terminal disclaimer.

[21] Appl. No.: 09/299,319

[22] Filed: Apr. 26, 1999

Related U.S. Application Data

[63] Continuation of application No. 09/063,465, Apr. 20, 1998, Pat. No. 5,935,930, which is a continuation of application No. 08/644,290, May 10, 1996, Pat. No. 5,741,779.

[51] Int. Cl.$^7$ .......................... A61K 38/00; A61K 38/16

[52] U.S. Cl. ............................ 514/12; 514/21; 514/822; 530/324; 530/350; 530/829; 424/529; 424/532

[58] Field of Search .................. 514/12, 21, 822; 530/324, 350, 829; 424/529, 532

[56] References Cited

U.S. PATENT DOCUMENTS

| | | | |
|---|---|---|---|
| 5,089,274 | 2/1992 | Marra et al. | 424/534 |
| 5,171,739 | 12/1992 | Scott et al. | 514/12 |
| 5,198,541 | 3/1993 | Elsbach et al. | 435/69.1 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |
| 5,420,019 | 5/1995 | Theofan et al. | 435/69.1 |
| 5,439,807 | 8/1995 | Grinna | 435/69.1 |
| 5,447,913 | 9/1995 | Ammons et al. | 514/12 |
| 5,466,580 | 11/1995 | White et al. | 435/7.1 |
| 5,466,581 | 11/1995 | White et al. | 435/7.32 |
| 5,488,034 | 1/1996 | McGregor et al. | 514/12 |
| 5,494,896 | 2/1996 | Hansbrough | 514/12 |
| 5,523,288 | 6/1996 | Cohen et al. | 514/12 |
| 5,532,216 | 7/1996 | Espevik et al. | 514/21 |
| 5,576,292 | 11/1996 | Elsbach et al. | 514/12 |
| 5,578,568 | 11/1996 | Ammons et al. | 514/12 |
| 5,578,572 | 11/1996 | Horwitz et al. | 514/12 |
| 5,741,779 | 4/1998 | White et al. | 514/12 |

FOREIGN PATENT DOCUMENTS

| | | |
|---|---|---|
| WO 90/09183 | 8/1990 | WIPO . |
| WO 92/03535 | 3/1992 | WIPO . |
| WO 92/09621 | 6/1992 | WIPO . |
| WO 93/05797 | 4/1993 | WIPO . |
| WO 93/23434 | 11/1993 | WIPO . |
| WO 93/23540 | 11/1993 | WIPO . |
| WO 93/23434 | 12/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |
| WO 94/20532 | 9/1994 | WIPO . |
| WO 94/21280 | 9/1994 | WIPO . |
| WO 94/25476 | 11/1994 | WIPO . |
| WO 95/01428 | 1/1995 | WIPO . |
| WO 95/02414 | 1/1995 | WIPO . |
| WO 95/07712 | 3/1995 | WIPO . |
| WO 95/08344 | 3/1995 | WIPO . |
| WO 95/08773 | 3/1995 | WIPO . |
| WO 95/10297 | 4/1995 | WIPO . |
| WO 95/19179 | 7/1995 | WIPO . |
| WO 95/19180 | 7/1995 | WIPO . |
| WO 95/19372 | 7/1995 | WIPO . |
| WO 95/19784 | 7/1995 | WIPO . |
| WO 95/24209 | 9/1995 | WIPO . |
| WO 96/01647 | 1/1996 | WIPO . |
| WO 96/08509 | 3/1996 | WIPO . |
| WO 96/21436 | 7/1996 | WIPO . |

OTHER PUBLICATIONS

Carr et al., "Granulocyte lysosomal cationic protein alters fibrin assembly: A possible mechanism for granulocyte control of clot structure," *J. Lab. Clin. Med.*, 107:199–203 (1986).

Carr et al., "Large Fibrin Fibers Enhance Urokinase–Induced Plasmin Digestion of Plasma Clots," *29th Ann. Meeting Am. Soc. Hematol., Blood*, 70(Suppl. 1):400a (1987).

Carr et al., "Platelet Factor 4 Enhances Fibrin Fiber Polymerization," *Thrombosis Research*, 45:539–543 (1987).

Carr et al., "Effects of Poloxamer 188 on the Assembly, Structure and Dissolution of Fibrin Clots," *Thrombosis and Haemostasis*, 66(5):565–568 (1991).

Cecil's Textbook of Medicine, 17th Edition, W.B. Saunders Co., Pennsylvania, pp. 1053–1058 (1985).

Chapter 52, "Coagulation Disorders," Cecil's Essentials of Medicine, 3rd Edition, W.B. Saunders Co., Pennsylvania, pp. 408–416 (1983).

Elsbach and Weiss, in *Inflammation: Basic Principles and Clinical Correlates*, Gallin et al., Eds., Chapter 30, Raven Press, Ltd. (1992).

Elsbach et al., "Separation and Purification of a Potent Bactericidal/Permeability Increasing Protein and a Closely Associated Phospholipase $A_2$ From Rabbit Polymorphonuclear Leukocytes," *J. Biol. Chem.*, 254(21):11000–11009 (1979).

Fears, R., "Kinetic studies on the effect of heparin and fibrin on plasminogen activators," *Biochem. J.*, 249:77–81 (1988).

Gazzano–Santoro et al., "High–Affinity Binding of the Bactericidal/Permeability–Increasing Protein and a Recombinant Amino–Terminal Fragment to the Lipid A Region of Lipopolysaccharide," *Infect. Immun.* 60(11):4754–4761 (1992).

Gray et al., "Cloning of the cDNA of a Human Neutrophil Bactericidal Protein," *J. Biol. Chem.*, 264(16):9505–9509 (1989).

Heyderman et al., "Is there a circulating anticoagulant in meningococcal disease," *Proc. Brit. Paediatric Association*, p. 40 (Abstract G13) (Apr. 17, 1991).

(List continued on next page.)

Primary Examiner—Christopher S. F. Low
Assistant Examiner—Abdel A. Mohamed
Attorney, Agent, or Firm—Marshall, O'Toole, Gerstein, Murray & Borun

[57] ABSTRACT

Antithrombotic materials and methods are provided for the treatment of thrombotic disorders, in which therapeutically effective amounts of BPI protein products are administered.

6 Claims, No Drawings

OTHER PUBLICATIONS

Hogg and Jackson, "Fibrin monomer protects thrombin from inactivation by heparin–antithrombin III: Implications for heparin efficacy," *Proc. Nat'l Acad. Sci., USA*, 86:3619–3623 (1989).

Hogg and Jackson, "Formation of a Ternary Complex between Thrombin, Fibrin Monomer, and Heparin Influences the Action of Thrombin on Its Substrates," *J. Biol. Chem.*, 265(1):248–255 (1990).

Hogg and Jackson, "Heparin Promotes the Binding of Thrombin to Fibrin Polymer," *J. Biol. Chem.*, 265(1):241–247 (1990).

Klement et al., "The Effect of Thrombin Inhibitors on Tissue Plasminogen Activator Induced Thrombolysis in a Rat Model," *Thrombosis & Haemostasis*, 68:64–68 (1992).

Majerus et al., Chapter 54, "Anticoagulant, Thrombolytic and Antiplatelet Drugs," Goodman & Gilman, The Pharmacological Basis of Therapeutics, 9th Edition, McGraw–Hill, NY, pp. 1341–1358 (1996).

Nenci et al., "Fibrin clots obtained from plasma containing heparin show a higher sensitivity to t–PA–induced lysis," *Blood Coagulation and Fibrinolysis*, 3:279–285 (1992).

Odrljin et al., "Thrombin Cleavage Enhances Exposure of a Heparin Binding Domain in the N–Terminus of the Fibrin β Chain," *Blood*, 88(6):2050–2061 (1996).

Ooi et al., "A 25–kDa $NH_2$–Terminal Fragment Carries All the Antibacterial Activities of the Human Neutrophil 60–kDa Bactericidal/Permeability–Increasing Protein," *J. Biol. Chem.*, 262(31):14891–14894 (1987).

Ooi et al., "Endotoxin Neutralizing Properties of the 25 kD N–Terminal Fragment of the 55–60 kD Bactericidal/Permeability–Increasing Protein of Human Neutrophils," *J. Exp. Med.*, 174:649–655 (1991).

Parise et al., "Effects of low molecular weight heparins on fibrin polymerization and clot sensitivity to t–PA–induced lysis," *Blood Coagulation and Fibrinolysis*, 4:721–727 (1993).

Retzinger et al., "Complexation with Heparin Prevents Adhesion between Fibrin–coated Surfaces," *J. Biol. Chem.*, 267(34):24356–24362 (1992).

Suffredini et al., "Promotion and Subsequent Inhibition of Plasminogen Activation After Administration of Intravenous Endotoxin to Normal Subjects," *New Engl. J. Med.*, 320(18):1165–1172 (1989).

von der Möhlen et al., "Inhibition of Endotoxin–Induced Activation of the Coagulation and Fibrinolytic Pathways Using a Recombinant Endotoxin–Binding Proetin ($rBPI_{23}$)," *Blood*, 85(12):3437–3443 (1995).

Weiss et al., "Cellular and Subcellular Localization of the Bactericidal/Permeability–Increasing Protein of Neutrophils," *Blood*, 69(2):652–659 (1987).

Bode et al., "Combinations of thrombolytic agents in acute myocardial infarction," *Zeitschnift for Kardiologie*, vol. 82 (Suppl. 2) 125–128 (1993).

Olsson et al., "Early Intravenous Beta Blockade and Thrombolytics in Acute Myocardial Infarction," *Amer. J. Cardiology*, vol. 72, No. 19 156G–169G (1993).

ANTITHROMBOTIC MATERIALS AND METHODS

This is a continuation of U.S. application Ser. No. 09/063,465, filed Apr. 20, 1998 now U.S. Pat. No. 5,935,930 which is a continuation of U.S. Ser. No. 08/644,290, filed May 10, 1996, now U.S. Pat. No. 5,741,779.

BACKGROUND OF THE INVENTION

The present invention relates generally to therapeutic compositions and treatment methods utilizing bactericidal/permeability-increasing protein (BPI) protein products for the treatment of thrombotic disorders.

The coagulation, or blood clotting process is involved both in normal hemostasis, in which the clot stops blood loss from a damaged blood vessel, and in abnormal thrombosis, in which the clot blocks circulation through a blood vessel. During normal hemostasis, the platelets adhere to the injured blood vessel and aggregate to form the primary hemostatic plug. The platelets then stimulate local activation of plasma coagulation factors, leading to generation of a fibrin clot that reinforces the platelet aggregate. Later, as wound healing occurs, the platelet aggregate and fibrin clot are degraded by specifically activated proteinases. During the pathological process of thrombosis, the same mechanisms create a platelet/fibrin clot that occludes a blood vessel. Arterial thrombosis may produce ischemic necrosis of the tissue supplied by the artery, e.g., myocardial infarction due to thrombosis of a coronary artery, or stroke due to thrombosis of a cerebral artery. Venous thrombosis may cause the tissues drained by the vein to become edematous and inflamed, and thrombosis of a deep vein may result in a pulmonary embolism.

An increased tendency toward thrombosis accompanies surgery, trauma, many inflammatory disorders, malignancy, pregnancy, obesity, vascular disorders and prolonged immobilization. Inherited thrombotic tendencies, which are much rarer, are being increasingly recognized and include deficiencies of the protein C-protein S system, deficiencies of antithrombin III (ATIII), dysfibrinogenemias, and other disorders of the fibrinolytic system. The evaluation of hypercoagulable risk involves checking for a family history of thromboembolism, and for other systemic predisposing diseases or conditions that favor localized vascular stasis (such as prolonged immobilization, pregnancy, or malignancy) and evaluating possible laboratory abnormalities, such as thrombocytosis, elevated blood or plasma viscosity, and elevated plasma levels of coagulation factors or fibrin degradation products. Levels of ATIII, protein C, or protein S levels, may also be measured, although hypercoagulability due to such abnormalities is uncommon compared to factors such as stasis or localized injury.

Severe derangements of the coagulation process are seen in disseminated intravascular coagulation (DIC), a syndrome characterized by the slow formation of fibrin microthrombi in the microcirculation and the development of concomitant fibrinolysis. The net result of these processes is the consumption of platelets and clotting factors in the thrombotic process, and the proteolytic digestion of several clotting factors by the fibrinolytic process, leading to decreased coagulability of the patient's blood. DIC never occurs as a primary disorder; it is always secondary to another disorder. These primary disorders fall into three general categories: (1) release of procoagulant substances into the blood, as may occur in amniotic fluid embolism, abruptio placentae, certain snake bites, and various malignancies, (2) contact of blood with an injured or abnormal surface, as may occur in extensive burns, infections, heat stroke, organ grafts, and during extracorporal circulation, and (3) generation of procoagulant-active substances within the blood, as may occur if red or white blood cell or platelet membranes become damaged and release thromboplastic substances, e.g., during leukemia treatment, hemolytic transfusion reactions and microangiopathic hemolytic anemia. Bacterial endotoxins on, associated with or released from gram-negative bacteria also have thromboplastin-like properties that initiate clotting.

Intravascular clotting occurs most frequently with shock, sepsis, cancer, obstetric complications, burns, and liver disease. There are no specific symptoms or signs unique to DIC. Bleeding, however, is much more evident than thrombosis. The rate and extent of clotting factor activation and consumption, the concentration of naturally occurring inhibitors, and the level of fibrinolytic activity determine the severity of the bleeding tendency. In some patients there is no clinical evidence of bleeding or thrombosis, and the syndrome becomes apparent only as a consequence of abnormal blood coagulation tests. Many patients develop only a few petechiae and ecchymotic areas and bleed a little more than usual from venipuncture sites. More pronounced forms of diffuse intravascular clotting may become evident as a result of severe gastrointestinal hemorrhage or genitourinary bleeding. In some instances bleeding may cause death. Hemorrhage caused by the DIC syndrome can be especially life threatening in association with obstetric complications or in conjunction with surgery.

The endpoint of the coagulation process is the generation of a powerful serine protease, thrombin, which cleaves the soluble plasma protein fibrinogen so that an insoluble meshwork of fibrin strands develops, enmeshing red cells and platelets to form a stable clot. This coagulation process can be triggered by injury to the blood vessels and involves the rapid, highly controlled interaction of more than 20 different coagulation factors and other proteins to amplify the initial activation of a few molecules to an appropriately sized, fully developed clot. Most of the coagulation proteins are serine proteases that show a high degree of homology (Factors II, VII, IX, and X); others are cofactors without enzyme activity (Factors V and VIII). These proteins circulate as inactive zymogens in amounts far greater than are required for blood clotting. Both the injured vessel wall and platelet aggregates provide specialized surfaces that localize and catalyze the coagulation reactions.

The coagulation cascade can be initiated via two different activation pathways: the intrinsic pathway, involving contact with injured tissue or other surfaces, and the extrinsic pathway, involving tissue factor expressed on injured or inflamed tissue. Both pathways converge into a common pathway when Factor X is activated at the platelet surface. [See, e.g., Cecil's Essentials of Medicine, 3rd ed., WB Saunders Co., Pennsylvania (1983); Goodman & Gilman, The Pharmacological Basis of Therapeutics, 9th ed., McGraw-Hill, N.Y. (1996).] The intrinsic pathway begins when Factor XII is activated to XIIa by contact with the altered or injured blood vessel surface or with another negatively charged surface, such as a glass tube. Cofactors or promoters of Factor XII activation include prekallikrein, high molecular weight kininogen, and Factor XI. These proteins form a surface-localized complex which optimally activates Factor XII. The activated Factor XIIa then converts the complex-bound Factor XI to its active form, XIa, and also converts prekallikrein to its active form, kallikrein, which then cleaves high molecular weight kininogen to form bradykinin. In turn, Factor XIa requires calcium ions ($Ca^{2+}$) to activate Factor IX to IXa. Factor XIa may also activate Factor VII (in the extrinsic pathway) as well. Activated Factor XIa also cleaves plasminogen to form plasmin, which is the main protease involved in the fibrinolytic mechanisms that restrain blood clotting. In the presence of $Ca^{2+}$ and phospholipid, Factor IXa activates Factor X to Xa, which is the first step in the common pathway. Factor X activation usually takes place at the plasma membrane of stimulated platelets but also may occur on the vascular endothelium.

In the extrinsic pathway, the release of tissue factor from injured tissues directly activates Factor VII to VIIa. Tissue factor is present in activated endothelium and monocytes as well as in brain, vascular adventitia, skin, and mucosa. Factor VIIa then activates Factor X to Xa in the presence of $Ca^{2+}$. In addition, the tissue factor, Factor VII, and $Ca^{2+}$ form a complex that can activate Factor IX (in the intrinsic pathway).

The activated Factor Xa (the first step in the common pathway) then activates prothrombin (Factor II) to generate the protease thrombin. Assembly of the plasma prothrombinase complex on the surface of activated platelets in the presence of Factor V, another cofactor, enhances the efficiency of prothrombin activation to thrombin on the platelet surface. Thrombin cleaves fibrinogen, which is a large, asymmetric, soluble protein with a molecular weight of about 340 kilodaltons consisting of three pairs of polypeptide chains: A$\alpha$, B$\beta$, and $\gamma$. Thrombin first removes small peptides from the A$\alpha$ chain of fibrinogen to form Fibrin I, which polymerizes end to end; further thrombin cleavage of small peptides from the B$\beta$ chain leads to formation of Fibrin II molecules, which polymerize side to side and are then cross-linked via the $\gamma$ subunits by the plasma glutaminase (Factor XIII) to form an insoluble fibrin clot.

Thrombin has multiple critical actions during coagulation in addition to the cleavage of fibrinogen to fibrin. It activates platelets, exposing their procoagulant activity (e.g., binding sites for the prothrombinase complex) and induces the release of platelet-aggregating substances such as thromboxane, $Ca^{2+}$, ADP, von Willebrand factor, fibronectin, and thrombospondin. Thrombin cleaves Factors VIII and Va, thus augmenting the coagulation cascade, and also cleaves plasma glutaminase, the enzyme which cross-links fibrin and stabilizes the fibrin clot. Thrombin acts on the endothelium by binding to the surface protein thrombomodulin to activate protein C, which is a potent inactivator of Factors Va and VIII and also stimulates fibrinolysis. Thrombin also causes endothelial cell contraction. Conversely, endothelium can bind and inactivate thrombin, and in some cases can generate the vasodilatory substance prostacyclin in response to thrombin. Thus, thrombin activation contributes to the limitation as well as the initiation of clotting.

There are two commonly used tests for measuring the coagulability of blood: the activated partial thromboplastin time (APTT or PTT) and the prothrombin time (PT). Blood generally clots in vitro in four to eight minutes when placed in a glass tube. Clotting is prevented if a chelating agent such as ethylenediaminetetraacetic acid (EDTA) or citrate is added to bind $Ca^{2+}$. Recalcified plasma, i.e., plasma in which $Ca^{2+}$ has been replenished, clots in two to four minutes. The clotting time after recalcification is shortened to 26 to 33 seconds by the addition of negatively charged phospholipids and a particulate substance such as kaolin (aluminum silicate); this post-recalcification clotting time is the APTT. Alternatively, recalcified plasma will clot in 12 to 14 seconds after addition of "thromboplastin," a saline extract of brain that contains tissue factor and phospholipids; this post-recalcification clotting time is the PT.

An individual with a prolonged APTT and a normal PT is considered to have a defect in the intrinsic coagulation pathway, because all of the components of the APTT test (except kaolin) are intrinsic to the plasma. A patient with a prolonged PT and a normal APTT has a defect in the extrinsic coagulation pathway, since thromboplastin is extrinsic to the plasma. Prolongation of both the APTT and the PT suggests a defect in a common pathway.

Whereas the blood coagulation pathways involve a series of enzymatic activations of serine protease zymogens, downregulation of blood clotting is influenced by a variety of natural anticoagulant mechanisms, including antithrombin III (ATIII), the protein C-protein S system, and fibrinolysis. Normal vascular endothelium promotes the activation of these anticoagulant mechanisms by acting as a source of heparin-like substances that enhance ATIII activation, a source of thrombomodulin, a cofactor in protein C activation, and a source of the tissue plasminogen activators that initiate fibrinolysis.

The anticoagulant ATIII is a plasma protease inhibitor that is specific for plasmin, the enzyme that dissolves clots. ATIII also binds all the serine protease procoagulant proteins (Factor Xa as well as thrombin). Complexes of ATIII and protease are rapidly cleared by the liver and the reticuloendothelial system. The activity of ATIII is enhanced by heparin or heparin-like substances. Other enzymes that play a role in limiting the coagulation process include the non-specific plasma protease inhibitors $\alpha_1$-antitrypsin, $\alpha_2$-plasmin inhibitor, and $\alpha_2$-macroglobulin, which rapidly inactivate any circulating serine proteases including thrombin and plasmin.

The final stage of the coagulation process is fibrinolysis, or clot dissolution. The endpoint of the fibrinolytic system is the generation of the enzyme plasmin, which dissolves intravascular clots by digesting fibrin. Fibrinolysis is initiated during clotting by the action of thrombin. When complexed to thrombomodulin in the endothelium, thrombin activates protein C, which initiates the release of tissue plasminogen activator (tPA) from the blood vessel wall. Protein C, together with its cofactor protein S, also inactivates Factors Va and VIIIa, thus dampening the coagulation cascade. The tPA then cleaves a circulating proenzyme, plasminogen, to form the active protease, plasmin, which digests fibrin. Plasmin is a relatively nonspecific protease; it not only digests fibrin clots but also digests other plasma proteins, including several coagulation factors.

The fibrinolytic system is regulated in a manner so that unwanted fibrin thrombi are removed, while fibrin in wounds persists to maintain hemostasis. The tPA is released from endothelial cells in response to various signals, including stasis produced by occlusion of the blood vessel. This released tPA exerts little effect on circulating plasminogen because tPA is rapidly cleared from blood or inhibited by circulating inhibitors, plasminogen activator inhibitor-1 and plasminogen activator inhibitor-2. Both plasminogen and its activator tPA bind to fibrin. The activity of tPA is actually enhanced by this binding to fibrin, so that the generation of plasmin is localized to the vicinity of the blood clot. In addition, fibrin-bound plasmin is protected from inhibition.

Four main types of therapies are used to prevent or treat thrombosis: antiplatelet agents, anticoagulant agents (heparin), vitamin K antagonists (coumarin derivatives) and thrombolytic agents. Each type of agent interferes with clotting at a different site in the coagulation pathway [See, generally, Goodman & Gilman, The Pharmacological Basis of Therapeutics, 9th ed., McGraw-Hill, N.Y. (1996).] Dipyridamole is another agent sometimes used to prevent or treat thrombosis; it is a vasodilator that, in combination with warfarin (a coumarin derivative), inhibits embolization from prosthetic heart valves and, in combination with aspirin, reduces thrombosis in patients with thrombotic disorders.

The antiplatelet agents include aspirin and other non-steroidal anti-inflammatory agents such as ibuprofen, which are all administered orally. Aspirin acts by irreversibly inhibiting platelet cyclooxygenase and thus blocking production of thromboxane $A_2$, an inducer of platelet aggregation and potent vasoconstrictor. In general, antiplatelet agents are used as prophylaxis against arterial thrombosis, because platelets are more important in initiating arterial than venous thrombi. Antiplatelet therapy also reduces the risk of occlusion of saphenous vein bypass grafts.

The anticoagulant agents include heparin and its derivatives, which act by accelerating the activities of ATIII in inhibiting thrombin generation and in antagonizing thrombin's action. Low molecular weight preparations of heparin such as dalteparin and enoxaparin may also be effective for anticoagulation. Heparin increases the rate of the thrombin-antithrombin reaction at least a thousandfold by serving as a catalytic template. Heparin can only be administered parenterally and has an immediate anticoagulant effect. It is used to prevent and treat arterial and venous thrombosis, as well as to keep blood fluid during extracorporeal circulation, such as with renal hemodialysis or during cardiopulmonary bypass, and to keep vascular access catheters patent. Heparin therapy is also standard in patients undergoing percutaneous transluminal coronary angioplasty.

Bleeding is the primary adverse effect of heparin. Major bleeding occurs in 1% to 33% of patients who receive various forms of heparin therapy. Purpura, ecchymoses, hematomas, gastrointestinal hemorrhage, hematuria, and retroperitoneal bleeding are regularly encountered complications of heparin therapy. Frequently bleeding is most pronounced at sites of invasive procedures. If bleeding is severe, the effects of heparin can be counteracted by giving 1 mg of protamine sulfate for each 100 units of heparin. Another side effect, thrombocytopenia, also occurs in 1% to 5% of patients receiving heparin, but subsides when heparin is discontinued.

The vitamin K antagonists (coumarin derivatives) are sometimes referred to as oral anticoagulants although they do not actually directly inhibit the coagulation cascade. These agents include 4-hydroxycoumarin, warfarin sodium, dicumarol, phenprocoumon, indan-1,3-dione, acenocoumarol, and anisindione. They interfere with the hepatic synthesis of Factors II, VII, IX, and X and proteins C and S, which are all involved in the coagulation process, and therefore have a slow onset of anticoagulant effect that spans several days. They are given orally; once the dose is established for an individual patient, they can provide a steady level of anticoagulation. Vitamin K antagonists are used for both the prevention and treatment of arterial and venous thrombosis.

Bleeding is the major adverse effect of vitamin K antagonists. Especially serious episodes involve sites where irreversible damage may result from compression of vital structures (e.g., intracranial, pericardial, nerve sheath, or spinal cord) or from massive internal blood loss that may not be diagnosed rapidly (e.g., gastrointestinal, intraperitoneal, retroperitoneal). The risk of intracerebral or subdural hematoma in patients over 50 years of age taking an oral anticoagulant over a long term may be increased ten-fold. For continued or serious bleeding, vitamin $K_1$ (phytonadione) is an effective antidote. Since reversal of anticoagulation by vitamin $K_1$ requires the synthesis of fully carboxylated coagulation proteins, significant improvement in hemostasis does not occur for several hours, regardless of the route of administration, and 24 hours or longer may be needed for maximal effect. Warfarin is contraindicated in women who are or may become pregnant because the drug passes through placental barrier and may cause fatal hemorrhage in the fetus. Warfarin treatment during pregnancy may also cause spontaneous abortion, still birth and birth defects.

The thrombolytic agents include tPA, streptokinase, urokinase prourokinase, anisolylated plasminogen streptokinase activation complex (APSAC), and animal salivary gland plasminogen activators, all of which act by accelerating fibrinolysis. The thrombolytic drugs are used to lyse freshly formed arterial and venous thrombi; they are not efficacious in dissolving thrombi that have been present for more than a few hours. The intravenous administration of these agents is now accepted as useful therapy in the management of deep vein thrombosis, pulmonary embolism, acute myocardial infarction, and peripheral arterial thromboembolism.

The major toxicity of all thrombolytic agents is hemorrhage, which results from two factors. Therapy with thrombolytic drugs tends to dissolve both pathological thrombi and fibrin deposits at sites of vascular injury. In addition, a systemic lytic state results from systemic formation of plasmin, which produces fibrinogenolysis and destruction of other coagulation factors. Massive fibrinolysis is initiated, and the inhibitory controls of the process are overwhelmed. The systemic loss of fibrinogen and platelet dysfunction caused by the thrombolytic agents also produces a hemorrhagic tendency. Thus, the use of thrombolytic agents is contraindicated in situations where there is active bleeding or a risk of major hemorrhage.

If heparin is used concurrently with either streptokinase or t-PA, serious hemorrhage will occur in 2% to 4% of patients. Intracranial hemorrhage is by far the most serious problem; it occurs in approximately 1% of cases, and the frequency is the same with all three thrombolytic agents. Retroperitoneal hemorrhage is also a serious complication. The frequency of hemorrhage is less when thrombolytic agents are utilized to treat myocardial infarction compared with pulmonary embolism or venous thrombosis; this difference may be due to the duration of therapy (1 to 3 hours for myocardial infarction, compared to 12 to 72 hours for pulmonary embolism and venous thrombosis).

In general, venous thrombosis and its potential for life-threatening pulmonary embolism are prevented and treated with heparin or warfarin. Low-dose subcutaneous heparin is frequently used as prophylaxis against venous thrombosis in surgical patients but is ineffective in those at highest risk, for example, after hip fracture. Warfarin reduces mortality from pulmonary embolism and can be given more safely to immobilized or post-surgical patients in low-dose or step-wise regimens. Once a venous thrombosis has developed, however, full-dose heparin treatment for 5 to 10 days overlapping with full-dose warfarin treatment for 4 to 5 days is necessary to prevent clot progression and/or pulmonary embolism. Thrombolytic agents have been used to treat pulmonary embolism and deep venous thrombosis, but their efficacy in reducing mortality remains to be established. Aspirin offers little value in treating venous thromboembolism.

For acute arterial thrombosis, thrombolytic therapy is generally the treatment of choice. The goals of thrombolytic therapy are to achieve rapid reperfusion of the thrombosed vessel and maintain patency of the vessel; these objectives are based on the premise that rapid and sustained restoration of blood flow reduces associated complications. However, multiple episodes of vessel reocclusion typically follow thrombolytic therapy. Although widely used as an adjunct to thrombolytic therapy, heparin does not accelerate thrombolysis or prevent reocclusion of the vessel. [Klement et al., Thrombosis Haemostasis, 68:64–68 (1992).] In patients with a fresh coronary thrombosis, intravenous thrombolytic therapy can permit rapid reperfusion of the thrombosed coronary artery, thus preserving cardiac function and reducing mortality, if administered within a few hours of the onset of symptoms. Thrombolytic agents can also re-establish the patency of thrombosed peripheral arteries if administered within a few hours after acute thrombosis. In some instances, e.g., for coronary artery thrombosis, the thrombolytic agent is administered locally by selective catheterization of the involved vessel. When given systemically rather than locally, a therapeutic effect is evident if the thrombin time is greater than twice normal. Such treatment should generally be followed by heparin and then oral anticoagulants to prevent further clot promulgation or recurrence. Following thrombolytic therapy and before the thrombin time has returned to its normal range, heparin is generally given to fully anticoagulate the patient for five to ten days. Warfarin may be started before the heparin is stopped, depending on whether prolonged anticoagulation will be required in the management of the patient's disorder. Aspirin is ineffective in the immediate setting, but is useful for long-term prophylaxis against arterial thrombosis. Recent studies suggest that the concurrent administration of low doses of aspirin improves the efficacy of thrombolytic therapy of myocardial infarction. Patients with symptomatic strokes are acutely anticoagulated with heparin and followed indefinitely with warfarin. Aspirin is recommended for prophylaxis of stroke in patients with cervical bruits, asymptomatic carotid stenosis, or a history of transient ischemic attacks and minor stroke.

Considerable controversy continues to surround the use of heparin in DIC. Heparin is usually reserved for fulminant, explosive forms of diffuse intravascular clotting, in which massive defibrination is accompanied by fibrinogen levels of less than 100 mg/dL and replacement therapy is not controlling the hemorrhage. In these cases, heparin is given as a continuous intravenous infusion at a rate of 10 to 15 units/kg/hour. If the patient is in immediate danger of dying from hemorrhage, 5000 to 10,000 units of heparin are given intravenously as a bolus and heparin is then continued at an infusion rate of 1000 units per hour.

Heparin can also be useful in treating unstable angina and patients undergoing elective cardioversion for atrial fibrillation of greater than 2 days duration. Warfarin and aspirin are useful for prophylaxis of cerebral embolism, particularly in patients at risk because of atrial fibrillation. More than 50% of patients with cerebral embolism have atrial fibrillation. Warfarin is also recommended for treating patients with mechanical heart valves, for whom the associated risk of embolism is 2% to 6% per patient per year despite anticoagulation, patients with rheumatic mitral valve disease, in whom the rate of associated thromboembolic complications is 1.5% to 4.7% per year, and patients with a history of thromboembolism. Aspirin is recommended for patients with mitral valve prolapse.

Anti-thrombotic agents are also used routinely to prevent the occlusion of extracorporeal devices: intravascular cannulas (heparin), vascular access shunts in hemodialysis patients (aspirin), hemodialysis machines (heparin), and cardiopulmonary bypass machines (heparin). In addition, they have been utilized in the treatment of certain renal diseases (heparin/warfarin) and small-cell lung cancer (warfarin).

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, J. Biol. Chem., 254:11000 (1979)] or E. coil affinity chromatography [Weiss, et al., Blood, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., J. Biol. Chem., 264:9505 (1989), incorporated herein by reference. The Gray et al. amino acid sequence is set out in SEQ ID NO: 1 hereto. U.S. Pat. No. 5,198,541 discloses recombinant genes encoding and methods for expression of BPI proteins, including BPI holoprotein and fragments of BPI.

BPI is a strongly cationic protein. The N-terninal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD possesses essentially all the anti-bacterial efficacy of the naturally-derived 55 kD human BPI holoprotein. [Ooi et al., J. Bio. Chem., 262: 14891–14894 (1987)]. In contrast to the N-terminal portion, the C-terminal region of the isolated human BPI protein displays only slightly detectable anti-bacterial activity against gram-negative organisms. [Ooi et al., J. Exp. Med., 174:649 (1991).] An N-terminal BPI fragment of approximately 23 kD, referred to as "rBPI$_{23}$," has been produced by recombinant means and also retains anti-bacterial activity against gram-negative organisms as well as endotoxin-neutralizing activity. [Gazzano-Santoro et al., Infect. Immun. 60:4754–4761 (1992).]

The bactericidal effect of BPI has been reported to be highly specific to gram-negative species, e.g., in Elsbach and Weiss, Inflammation: Basic Principles and Clinical Correlates, eds. Gallin et al., Chapter 30, Raven Press, ltd. (1992). The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. LPS has been referred to as "endotoxin" because of the potent inflammatory response that it stimulates, i.e., the release of mediators by host inflammatory cells which may ultimately result in irreversible endotoxic shock. BPI binds to and neutralizes lipid A, reported to be the most toxic and most biologically active component of LPS.

In addition to BPI's bactericidal and endotoxin binding/neutralizing activities, BPI has been shown to bind and neutralize heparin. Co-owned U.S. Pat. No. 5,348,942 was issued Sept. 20, 1994 with claims directed to methods of neutralizing the anticoagulant effects of heparin with BPI protein products (i.e., their procoagulant activity). There has been no suggestion or use of BPI as an anticoagulant or thrombolytic agent, nor any suggestion of its use for the prophylaxis or treatment of thrombotic disorders.

There exists a need in the art for methods and compositions capable of exerting anticoagulant or thrombolytic effects without severe adverse side effects, and methods and compositions capable of improving the therapeutic effectiveness of existing anticoagulant or thrombolytic agents, which ideally could reduce the required dosages of such existing agents.

SUMMARY OF THE INVENTION

The present invention provides novel methods for slowing clot formation and for enhancing clot dissolution using BPI protein products, and further provides methods for treatment of thrombotic disorders by administration of BPI protein products in therapeutically effective amounts.

According to the invention, a BPI protein product such as $rBPI_{21}$ is administered to a subject suffering from thrombotic disorder in an amount effective to treat such disorder, including prophylactic and therapeutic treatment. BPI protein products reduce the adverse effects of thrombotic disorder by activities that include slowing or delaying clot formation (i.e., anticoagulant activity) or by enhancing, accelerating or increasing clot dissolution (i.e., thrombolytic activity).

In another aspect of the invention, methods are provided for the treatment of thrombotic disorder by concurrent administration of a BPI protein product with a thrombolytic agent, including tPA, streptokinase, urokinase, prourokinase, APSAC, animal salivary gland plasminogen activators, other plasminogen activators, and derivatives of such plasminogen activators. According to this aspect of the invention, the thrombolytic agent dissolves the clot, while the BPI protein product enhances the dissolution activity of the thrombolytic agent and/or delays clot formation, thus delaying, decreasing or preventing rethrombosis. The BPI protein products are effective with both endogenous levels and therapeutic levels of thrombolytic agents such as plasminogen activators.

This aspect of the invention also provides methods for decreasing the dose of a thrombolytic agent required for a desired therapeutic or prophylactic effect in a patient, such as for dissolving a blood clot, by concurrent administration of BPI protein product and the thrombolytic agent.

The invention further provides methods for accelerating reperfusion and/or delaying or preventing reocclusions in a subject treated with a thrombolytic agent, e.g., tPA, by concurrent administration of BPI protein product with the thrombolytic agent.

As will be appreciated from the following detailed description, methods of the present invention provide safer and more effective treatment of thrombotic disorders than conventional therapies. By reducing the dosage of antithrombotic agent required to achieve a desired therapeutic effect, BPI protein products can reduce or eliminate the potential side effects often associated with conventional antithrombotic agent therapies, while not interfering with the antithrombotic activity of those agents. Importantly, use of such BPI protein products can enhance the antithrombotic activity of such agents by slowing clot formation or enhancing clot dissolution.

Numerous additional aspects and advantages of the invention will become apparent to those skilled in the art upon consideration of the following detailed description of the invention which describes presently prepared embodiments thereof.

DETAILED DESCRIPTION OF THE INVENTION

Thrombotic disorders, including acute vascular diseases, such as myocardial infarction, stroke, peripheral arterial occlusion, deep vein thrombosis, pulmonary embolism, and other blood system thromboses, constitute major health risks. Such disorders are caused by either partial or total occlusion of a blood vessel by a blood clot, which consists of fibrin and platelet aggregates. Therapeutic intervention with agents that prevent or delay clot formation (i.e., anticoagulants) or with agents that dissolve blood clots (i.e., thrombolytics) is associated with numerous limitations, complications, risks and side effects. Most significant are the bleeding side effects associated with therapeutic doses of such agents and the complications associated with rethrombosis and reocclusion following reperfusion. It has now been unexpectedly discovered that administration of BPI protein products effectively slows clot formation and enhances clot dissolution in blood. The administered BPI protein product present in the blood during clot formation delays clotting time and/or may change the character of the clot that is formed to a looser, less stable clot.

It is contemplated that BPI protein products may be administered alone or concurrently with other antithrombotic (anticoagulant or thrombolytic) agents. Anticoagulant agents are agents with the pharmacological effect of slowing clot formation, such as dalteparin and enoxaparin, the coumarin derivative oral anticoagulants such as warfarin, and aspirin. Thrombolytic agents are agents with the pharmacological effect of enhancing clot dissolution, and include plasminogen activators such as t-PA, streptokinase, urokinase, proutokinase, APSAC, animal salivary gland plasminogen activators and derivatives thereof.

BPI protein products used according to methods of the invention unexpectedly have the property of making blood clots more susceptible to dissolution or lysis either at endogenous levels or added levels of plasminogen activators, such as tPA. Whether the tPA is present prior to clot formation or after clot formation, the BPI protein product enhances clot dissolution, e.g., accelerates clot dissolution or lysis, or provides more complete clot dissolution or lysis. Thus, BPI protein products are useful in methods for the treatment of thrombotic disorders, for dissolving or lysing clots in thrombotic patients, for delaying or inhibiting hard clot formation or supplementing thrombolytic therapy in the patients.

The previously described biological activities of BPI protein products, including bactericidal, endotoxin binding and neutralizing, heparin binding and neutralizing activities, do not suggest or even hint at the anticoagulant or thrombolytic activities of BPI protein products and the therapeutic uses that arise from these unexpected and previously undiscovered activities. In particular, the activity of BPI protein products as agents for treatment of thrombotic disorders is particularly surprising in view of the previously discovered activity of BPI protein products to bind and neutralize heparin (see, co-assigned U.S. Pat. No. 5,348,942).

The term "treatment" as used herein encompasses both prophylactic and therapeutic treatment of thrombotic disorders.

The term "thrombotic disorder" as used herein encompasses conditions associated with or resulting from thrombosis or a tendency towards thrombosis. These conditions include conditions associated with arterial thrombosis, such as coronary artery thrombosis and resulting myocardial infarction, cerebral artery thrombosis or intracardiac thrombosis (due to, e.g., atrial fibrillation) and resulting stroke, and other peripheral arterial thrombosis and occlusion; conditions associated with venous thrombosis, such as deep venous thrombosis and pulmonary embolism; conditions associated with exposure of the patient's blood to a foreign or injured tissue surface, including diseased heart valves, mechanical heart valves, vascular grafts, and other extracorporeal devices such as intravascular cannulas, vascular access shunts in hemodialysis patients, hemodialysis machines and cardiopulmonary bypass machines; and conditions associated with coagulapathies, such as hypercoagulability and disseminated intravascular coagulopathy that are not the result of an endotoxin-initiated coagulation cascade.

"Concurrent administration," or "co-administration" or "co-treatment," as used herein includes administration of the agents, in conjunction or combination, together, or before or after each other. The BPI protein product and other antithrombotic (including anticoagulant or thrombolytic) agents may be administered by different routes. For example, the BPI protein product may be administered intravenously while the antithrombotic agent is administered intramuscularly, intravenously, subcutaneously or orally. Alternatively, the BPI protein product may be administered, e.g., in an aerosolized or nebulized form while the antithrombotic agent is administered, e.g., intravenously. The BPI protein product and antithrombotic agent are preferably both administered intravenously, in which case they may be given sequentially in the same intravenous line, or after an intermediate flush, or in different intravenous lines. The BPI protein product and antithrombotic agent may be administered simultaneously or sequentially, as long as they are given in a manner sufficient to allow both agents to achieve effective concentrations at the site of thrombosis. During sequential administration of BPI protein product and antithrombotic agent, it is also contemplated that a time period varying from minutes to hours may intervene between the administration of the agents.

Conventional antithrombotic agents are expected to be administered in dosages and by routes consistent with the usual clinical practice. The typical dosages and administration regimens for some of these anticoagulant and thrombolytic agents, when administered as monotherapy, are discussed below. Naturally, these dosages vary as determined by good medical practice and the clinical condition of the individual patient.

The dosing of warfarin must be individualized according to the patient's sensitivity to the drug as indicated by its effect on the prothrombin time (PT) ratio. The loading dose is typically 2 to 5 mg/day and most patients are satisfactorily maintained at a dose of 2 to 10 mg/day. Warfarin is generally given orally but may be administered intravenously if the patient cannot take the drug orally.

Urokinase is indicated for lysis of acute pulmonary emboli and coronary artery emboli, and is also used to restore patency to intravenous cannulae and catheters. The drug is typically administered in an initial dose of 2,000 units/lb over a period of 10 minutes followed by a continuous infusion of 2,000 units/lb/hr for 12 hours. The total dose of urokinase given will range from 2.25 million to 6.25 million units, depending on the weight of the patient. When it is used to clear intravenous cannulae or catheters, urokinase is given as a single injection of 5,000 units in a volume of 1 mL.

Streptokinase is indicated for use in the management of acute myocardial infarction, lysis of intracoronary thrombi, arterial thrombosis or embolism, deep vein thrombosis, pulmonary embolism, and for clearing blocked cannulae or catheters. For treatment of acute myocardial infarction, 1.5 million units may be given by intravenous infusion over 60 minutes. Alternatively, it may be given by intracoronary infusion of a 20,000 unit bolus followed by 2,000 units/min. over 60 minutes. For other non-myocardial infarction indications, a dosage of 250,000 units by intravenous infusion over 30 minutes is appropriate for the great majority of patients.

Anistreplase (also known as ASPAC) is generally administered in a single dose of 30 units by intravenous injection over 2 to 5 minutes. Its use is indicated in the management of acute myocardial infection and for the lysis of coronary artery thrombi.

The drug tPA is dosed based upon patient weight, with the total dose not exceeding 100 milligrams. For patients weighing more than 67 kg, the recommended dose is a 15 mg initial intravenous bolus followed by a continuous infusion of 15 mg over 30 minutes, and further followed by 35 mg infused over the next 60 minutes. For patients weighing less than or equal to 67 kg, the recommended dose is a 15 mg initial intravenous bolus followed by 0.75 mg/kg (not to exceed 50 mg) over 30 minutes, and further followed by 0.5 mg/kg (not to exceed 35 mg) over the following 60 minutes.

Therapeutic compositions comprising BPI protein product may be administered systemically or locally into the involved vessel. Systemic routes of administration include oral, intravenous, intramuscular or subcutaneous injection (including into a depot for long-term release), intraocular and retrobulbar, intrathecal, intraperitoneal (e.g., by intraperitoneal lavage), intrapulmonary using aerosolized or nebulized drug, or transdermal. The preferred systemic route is intravenous administration. In some instances, e.g., for coronary artery or peripheral artery thrombosis, it is advantageous to administer the BPI protein product regionally by selective catheterization of the involved vessel. When given parenterally, BPI protein product compositions are generally injected in doses ranging from 1 $\mu$g/kg to 100 mg/kg per day, preferably at doses ranging from 0.1 mg/kg to 20 mg/kg per day, and more preferably at doses ranging from 1 to 20 mg/kg/day. The treatment may continue by continuous infusion or intermittent injection or infusion, at the same, reduced or increased dose per day for as long as determined by the treating physician. Those skilled in the art can readily optimize effective dosages and monotherapeutic or concurrent administration regimens for BPI protein product and/or other antithrombotic agents, as determined by good medical practice and the clinical condition of the individual patient.

When BPI protein product is concurrently administered with antithrombotic agents, the BPI protein product and the antithrombotic agents may each be administered in amounts that would be sufficient for monotherapeutic effectiveness, or they may be administered in less than monotherapeutic amounts. It is expected that BPI protein products are capable of improving the therapeutic effectiveness of existing anticoagulant or thrombolytic agents, which would reduce the dosages needed to exert their desired anticoagulant or thrombolytic effects. This, in turn, decreases the risk of adverse side effects associated with the use of thrombolytic agents, including, for example, undesirable internal or external bleeding.

BPI protein products may improve the therapeutic effectiveness of other antithrombotic agents in a variety of ways.

For example, lowering the dosage of the antithrombotic agent required for therapeutic effectiveness reduces toxicity and/or cost of treatment, and thus allows wider use of the agent. Alternatively, concurrent administration may produce an increased, more rapid or more complete anticoagulant or thrombolytic effect than could be achieved with either agent alone.

It is further contemplated that BPI protein product compositions are useful, in vitro or in vivo in restoring or maintaining patency of cannulae, catheters and tubing obstructed by clotted blood or fibrin, in maintaining the anticoagulation of blood, e.g., in blood bags, and in maintaining blood fluidity in, e.g., hemodialysis and extracorporeal circulation, and around foreign implants, e.g., heart valves or prosthetics.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as $rBPI_{50}$ and recombinant fragments of BPI. Co-owned, copending U.S. patent application Ser. No. 07/885,501 and a continuation-in-part thereof, U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in co-owned and co-pending U.S. patent application Ser. No. 08/212,132, filed Mar. 11, 1994, and corresponding PCT Application No. PCT/US95/03125, the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064,693 filed May 19, 1993 and corresponding PCT Application No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof. Similarly configured hybrid fusion proteins involving part or all Lipopolysaccharide Binding Protein (LBP) are also contemplated for use in the present invention.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993 and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Other examples include dimeric forms of BPI analogs; e.g. co-owned and co-pending U.S. patent application Ser. No. 08/212,132 filed Mar. 11, 1994, and corresponding PCT Application No. PCT/US95/03125, the disclosures of which are incorporated herein by reference.

Other BPI protein products useful according to the methods of the invention are peptides derived from or based on BPI produced by recombinant or synthetic means (BPI-derived peptides), such as those described in co-owned and co-pending U.S. patent application Ser. No. 08/504,841 filed Jul. 20, 1995 and in co-owned and copending PCT Application No. PCT/US94/10427 filed Sept. 15, 1994, which corresponds to U.S. patent application Ser. No. 08/306,473 filed Sept. 15, 1994, and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993, the disclosures of all of which are incorporated herein by reference.

Presently preferred BPI protein products include recombinantly-produced N-terminal fragments of BPI, especially those having a molecular weight of approximately between 21 to 25 kD such as $rBPI_{21}$ or $rBPI_{23}$, or dimeric forms of these N-terminal fragments (e.g., $rBPI_{42}$ dimer). Additionally, preferred BPI protein products include $rBP_{50}$ and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-microbial agents. One pharmaceutical composition containing BPI protein products (e.g., $rBPI_{50}$, $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another pharmaceutical composition containing BPI protein products (e.g., $rBPI_{21}$) comprises the BPI protein product at a concentration of 2 mg/mL in 5 mM citrate, 150 mM NaCl, 0.2% poloxamer 188 and 0.002% polysorbate 80. Such combinations are described in co-owned, co-pending PCT Application No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

Other aspects and advantages of the present invention will be understood upon consideration of the following illustrative examples. Example 1 addresses the effects of BPI protein product on clot formation and clot lysis/dissolution under varying conditions in tube assays. Example 2 addresses the effects of BPI protein products on clot formation and clot lysis/dissolution, as monitored by turbidity measurements, under varying conditions in microtiter plate assays. Example 3 addresses the effects of BPI protein product in vivo in a rat thrombus model with concurrent administration of tPA.

EXAMPLE 1

EFFECTS OF BPI PROTEIN PRODUCT ON CLOT FORMATION AND CLOT LYSIS/DISSOLUTION

A tube assay was used to determine the effects of a BPI protein product on clot formation and on clot lysis or dissolution under a variety of conditions using human plasma samples. Unless otherwise noted the human plasma used in these assays was prepared from human blood drawn from a variety of donors into ACD VACUTAINER® tubes (Becton Dickinson, Mountainview, Calif.) containing citrate as an anticoagulant, and was stored frozen at −70° C. For the preparation of platelet rich plasma (PRP), the anticoagulated blood was centrifuged at approximately 180×g for 5 minutes and the plasma removed following this low-speed centrifugation. For the preparation of platelet poor plasma (PPP), the anticoagulated blood was centrifuged at approximately 460×g for 10 minutes and the plasma removed following this higher speed centrifugation.

In an initial experiment to determine whether BPI protein products interacted with plasma proteins, ACD plasma pooled from two human donors was passed over a column containing $rBPI_{23}$ that was conjugated to Sepharose via cyanogen bromide. Approximately 40 mL of plasma was passed through the $rBPI_{23}$-Sepharose column to allow binding of plasma components. The column was washed with phosphate buffered saline (10 mM phosphate, 0.15 M NaCl, pH 7.2) until the $OD_{280}$ of the wash was <0.02. The bound plasma components were eluted with high salt (1.5 M NaCl) and the protein eluate was analyzed by SDS-PAGE. Amino acid sequence analysis of several protein bands showed that prothrombin and fibrinogen were bound by $rBPI_{23}$.

The ability of exemplary BPI protein products to delay clot formation (i.e., anticoagulant activity) and/or to enhance the dissolution or lysis of a clot once formed (i.e., thrombolytic activity) was evaluated. Such anticoagulant and/or thrombolytic activity demonstrates the utility of BPI protein products for the treatment of thrombotic disorder in a subject suffering from such disorder. The effects of BPI protein products were evaluated in PPP and PRP under a variety of conditions as follows.

A. Effect of Different Surface Environments

Clot formation and lysis were evaluated in the presence and absence of $rBPI_{21}$ in polypropylene or glass test tubes. For all experiments in this and subsequent examples, the $rBPI_{21}$ used was formulated at 2 mg/mL in 5 mM citrate, 150 mM NaCl, 0.2% poloxamer 188 (Pluronic F-68, BASF Wyandotte, Parsippany, N.J.), and 0.002% polysorbate 80 (TWEEN 80, ICI Americas Inc., Wilmington, Del.). Other BPI protein products used herein were similarly formulated at 1 mg/mL. The 0.1% HSA-TBS used was 0.1% human serum albumin (HSA) [Alpha Therapeutics, Los Angeles, Calif.] in Tris-buffered saline (TBS) [0.02M Tris, 0.15 M NaCl, pH 7.4]. For the clot formation part of this experiment, the following reagents were mixed together in the following order: (1) 160 μL of PPP (Donor RL); (2) 40 μL of $rBPI_{21}$ (either 10 or 250 μg/mL in 0.1% HSA-TBS); and (3) 200 μL of 40 mM $CaCl_2$ in TBS, pH 7.8.

The tubes were allowed to stand at room temperature, and every 1 minute the tubes were checked by gently tipping the tube and visually inspecting it for clot formation. The time in minutes to clot formation after $CaCl_2$ addition was measured.

| Tube Type | Minutes to Clot Formation (After $CaCl_2$ Addition) | | |
|---|---|---|---|
| | Control (0.1% HSA-TBS) | $rBPI_{21}$ 1 μg/mL | $rBPI_{21}$ 25 μg/mL |
| Polypropylene | 12 | 14 | 24 |
| Glass | 6 | 6 | 9 |

Clot formation was faster in glass tubes than in polypropylene tubes. However, $rBPI_{21}$ prolonged clotting times in both glass and polypropylene tubes. The higher $rBPI_{21}$ concentration tested (25 μg/mL) produced the longest delay in clotting time.

For the clot dissolution part of this experiment, 33 minutes after $CaCl_2$ addition, 44 μL of tPA [Calbiochem, San Diego, Calif.] (600 units/mL, or 1 μg/mL) were added to each tube to provide a final tPA concentration of 60 units/mL (or 100 ng/mL). This is in the range of elevated endogenous concentrations observed for tPA in certain physiologic states/conditions [See, e.g., von der Möhlen et al., Blood, 85:3437–3443 (1995); Suffradini, et al., New Engl. J. Med., 320:1165–1172 (1989)]. The tubes were incubated for 10 minutes at room temperature, then placed in a 37° C. water bath. Each tube was checked for clot dissolution/lysis by visual inspection.

After 5 minutes, the $rBPI_{21}$-treated clots in glass tubes had detached from the sides of the tube while all other clots remained adhered to the side of the tube. At 3.5 hours the clot in the 25 µg/mL $rBPI_{21}$ polypropylene tube was smaller, approximately ⅓ the size of the clots in the 1 µg/mL $rBPI_{21}$ and control polypropylene tubes. Clot dissolution/lysis times were faster in glass than in polypropylene tubes. The presence of 25 µg/mL $rBPI_{21}$ accelerated the dissolution of the clot. In all subsequent experiments, polypropylene tubes were utilized to minimize the protein adsorption effects of the glass.

B. Effect of Calcium Ion Concentration

Clot formation and lysis were evaluated in the presence or absence of $rBPI_{21}$ with varying concentrations of calcium (10, 15, 20 mM) to determine optimum calcium concentration. For the clot formation part of this experiment, the following reagents were mixed together in a polypropylene test tube in the following order: (1) 60 µL of 0.1% HSA-TBS; (2) 100 µL of PPP (Donor PC); (3) 40 µL of $rBPI_{21}$ (either 10 or 250 µg/mL in 0.1% HSA-TBS); and (4) 200 µL of 20, 30, or 40 mM $CaCl_2$ in TBS, pH 7.8.

The tubes were allowed to stand at room temperature and were checked every 1 minute for gel clot formation by visual inspection. At all calcium concentrations tested, increased $rBPI_{21}$ concentrations correlated with increased clotting time. The higher $rBPI_{21}$ concentration produced the longest delay in clotting time.

For the clot dissolution part of this experiment, 35 minutes after $CaCl_2$ addition, 44 µL of tPA (600 units/mL, or 1 ng/mL) were added to each tube to provide a final tPA concentration of 60 units/mL or 100 µg/mL. The tubes were incubated in a 37° C. water bath and checked approximately every twenty minutes for clot dissolution/lysis by visual inspection.

$rBPI_{21}$ accelerated the dissolution of the clot. Again, this was most apparent at the 25 µg/mL $rBPI_{21}$ concentration. Optimal clot formation and clot lysis was observed using 10 mM calcium. In all subsequent experiments, 10 mM $CaCl_2$ was used for initiation of clotting and lysis.

C. Effect of Pre-Clot and Post-Clot Addition of tPA

Clot formation and lysis were evaluated in the presence or absence of $rBPI_{21}$ with pre-clot or post-clot addition of tPA. For the clot formation part of this experiment, the following reagents were mixed together in a polypropylene test tube in the following order: (1) 60 µL of 0.1% HSA-TBS; (2) 100 µL of PPP (Donor PC); (3) 40 µL of $rBPI_{21}$ (either 10 or 250 µg/mL in 0.1% HSA-TBS); (4) for pre-clot only, 44 µL of tPA (600 units/mL, or 100 ng/mL); and (5) 200 µL of 20 mM $CaCl_2$ in TBS, pH 7.8.

The tubes were allowed to stand at room temperature and were checked every 1 minute for gel clot formation by visual inspection. The time in minutes to clot formation after $CaCl_2$ addition were measured. A delay in clot formation was observed only for 25 µg/mL $rBPI_{21}$ with pre-clot tPA addition.

For the clot dissolution part of this experiment, 35 minutes after $CaCl_2$ addition, 44 µL of tPA (600 units/mL, or 1 µg/mL) were added to the post-clot tubes. The final tPA concentration in all tubes (pre- and post-clot) was 60 units/mL or 100 ng/mL. All tubes were incubated in a 37° C. water bath and checked approximately every twenty minutes for clot dissolution/lysis by visual inspection. Time to clot dissolution in hours (for post-clot addition of tPA) or in minutes (for pre-clot addition of tPA) was evaluated. In this experiment, clot lysis when the tPA was added pre-clot was at least 6 times faster than post-clot. The $rBPI_{21}$ at 25 µg/mL appeared to accelerate clot lysis time. Because of the unexpectedly rapid dissolution of the clot under conditions of pre-clot tPA addition, precise times for clot dissolution were not assessed in this experiment. These results demonstrated that clot lysis was dramatically accelerated by the addition of tPA prior to clot formation rather than after clot formation.

D. Effect of Pre-Clot Addition of Varying Concentrations of tPA

Clot formation and lysis were evaluated in the presence or absence of $rBPI_{21}$ with pre-clot addition of tPA to a final concentration of 0, 6, or 60 units/mL. For the clot formation final part of this experiment, the following reagents were mixed together in a polypropylene test tube in the following order: (1) 60 µL of 0.1% HSA-TBS; (2) 100 µL of PPP (Donor RL); (3) 40 µL of $rBPI_{21}$ (either 10 or 250 µg/mL in 0.1% HSA-TBS); (4) 44 µL of tPA (600 units/mL, or 100 ng/mL) or buffer control (0.1% HSA-TBS); and (5) 200 µL of 20 mM $CaCl_2$ in TBS, pH 7.8.

The tubes were allowed to stand at room temperature, and were checked every 1 minute for gel clot formation by visual inspection. The minutes to clot formation after $CaCl_2$ addition were measured. Adding increasing amounts of tPA (0, 6, 60 units/mL) did not significantly alter the time to clot formation for the conditions tested.

| tPA Concentration (units/mL) | Minutes to Clot Formation (After $CaCl_2$ Addition) | | |
|---|---|---|---|
| | Control (0.1% HSA-TBS) | $rBPI_{21}$ ~1 µg/mL | $rBPI_{21}$ ~25 µg/mL |
| 0 | 17 | 19 | 44 |
| 6 | 18 | 19 | 45 |
| 60 | 15 | 20 | 45 |

For the clot dissolution part of this experiment, 53 minutes after $CaCl_2$ addition, all tubes were placed in a 37° C. water bath and checked for clot dissolution/lysis by visual inspection. Time to clot dissolution in hours or minutes was evaluated. With no tPA, no clot lysis was observed. A tPA dose response effect was observed, with the higher tPA concentration (60 units/mL) producing the most rapid clot dissolution. Under these conditions with this donor's plasma, $rBPI_{21}$ had a much greater effect on the delay of clot formation while having minimal effect on clot dissolution. It is apparent that individual plasma donors can have significantly different clotting and dissolution times (compare results in parts A–C above). These differences could be due to different concentrations of crucial clotting factors in individual donor plasma.

E. Effect of $rBPI_{21}$ and tPA When Added Pre-Activation and Post-Activation

Clot formation and lysis were evaluated when both $rBPI_{21}$ and tPA were added prior to calcium addition (pre-activation or pre-calcium) and 4 minutes after calcium addition (post-activation or post-calcium). The following reagents were mixed together in a polypropylene test tube in the following order: (1) 60 µL of 0.1% HSA-TBS; (2) 100 µL of PPP (Donor PC); (3) 84 µL of $rBPI_{21}$ (either 5, 25 or 125 µg/mL) with tPA (300 units/mL, 50 ng/mL), or buffer control (0.1% HSA-TBS); and (4) 200 µL of 20 mM $CaCl_2$ in TBS, pH 7.8.

The tubes were allowed to stand at room temperature, and were checked every 1 minute for gel clot formation by visual inspection. The minutes to clot formation after $CaCl_2$ addition were measured.

| Timing of rBPI$_{21}$ and tPA addition | Minutes to Clot Formation (After CaCl$_2$ Addition) | | | |
|---|---|---|---|---|
| | Control (0.1% HSA-TBS) | rBPI$_{21}$ ~1 µg/mL | rBPI$_{21}$ ~5 µg/mL | rBPI$_{21}$ ~25 µg/mL |
| Pre-Calcium | 7 | 7 | 8 | 11 |
| 4 min Post-Calcium | 7 | 7 | 8 | 8 |

In this experiment, 25 µg/mL rBPI$_{21}$ slowed clot formation only when present prior to calcium addition. No significant effect was observed on rate of clot formation when the rBPI$_{21}$ was added 4 minutes after calcium addition.

For the clot dissolution part of this experiment, 15 minutes after CaCl$_2$ addition, all tubes were placed in a 37° C. water bath and checked approximately every minute for clot dissolution/lysis by visual inspection. The minutes to clot dissolution were measured.

| Timing of rBPI$_{21}$ and tPA addition | Minutes to Clot Lysis (After Placement in Water Bath) | | | |
|---|---|---|---|---|
| | Control (0.1% HSA-TBS) | rBPI$_{21}$ ~1 µg/mL | rBPI$_{21}$ ~5 µg/mL | rBPI$_{21}$ ~25 µg/mL |
| Pre-Calcium | 58 | 54 | 53 | 51 |
| 4 min Post-Calcium | 50 | 45 | 44 | 40 |

Clot dissolution appeared to be faster when rBPI$_{21}$ and tPA were added post-calcium compared to pre-calcium. A small rBPI$_{21}$ dose-response effect on clot dissolution was detected for both pre- and post-calcium groups. These results indicated that the timing of rBPI$_{21}$ and tPA addition relative to calcium addition (clot activation) influenced clot formation and dissolution.

In an additional experiment using higher plasma concentrations, clot formation and lysis were evaluated when rBPI$_{21}$ and tPA were added pre-calcium and 3 minutes post-calcium. The following reagents were mixed together in a polypropylene test tube in the following order: (1) 160 µL of PPP (Donor PC); (2) 84 µL of rBPI$_{21}$ (either 5, 25 or 125 µg/mL) with tPA (300 units/mL, or 50 ng/mL) or buffer control (0.1% HSA-TBS); and (3) 200 µL of 20 mM CaCl$_2$ in TBS, pH 7.8.

The tubes were allowed to stand at room temperature and were checked every 1 minute for gel clot formation by visual inspection. The minutes to clot formation after CaCl$_2$ addition were measured. In this experiment, 25 µg/mL rBPI$_{21}$ slowed clot formation (~50% prolongation) when present prior to calcium addition. A slight effect (~22% prolongation) was observed on clot formation when 25 µg/mL rBPI$_{21}$ was added 3 minutes after calcium addition.

For the clot dissolution part of this experiment, 15 minutes after CaCl$_2$ addition, all tubes were placed in a 37° C. water bath and checked for clot dissolution/lysis by visual inspection. The minutes to clot dissolution were measured. A small rBPI$_{21}$ dose-response effect on clot dissolution was again detected for both pre- and post-calcium addition groups. Only minimal differences in clot dissolution were observed between pre- and post-calcium addition of rBPI$_{21}$ and tPA. Although a larger difference in clot dissolution between pre- and post-calcium addition groups was observed in a previous experiment, that result may have been due to the different plasma concentration utilized. These results confirmed those of the previous experiments that the timing of rBPI$_{21}$ and tPA addition relative to calcium addition (clot activation), as well as plasma concentration, influenced clot formation and dissolution.

F. Effect of Clotting Temperature

Clot formation and lysis were evaluated at several clotting temperatures. For the clot formation part of this experiment, the following reagents were mixed together in a polypropylene test tube in the following order: (1) 60 µL of 0.1% HSA-TBS; (2) 100 µL of PPP (Donor PC); (3) 40 µL of rBPI$_{21}$ (either 10, 50 or 250 µg/mL) or buffer control; (4) 44 µL of tPA (600 units/mL, or 100 ng/mL) or buffer control (0.1% HSA-TBS); and (5) 200 µL of 20 mM CaCl$_2$ in TBS, pH 7.8.

The tubes were incubated at room temperature (R.T.) or 37° C. and were checked every 1 minute for gel clot formation by visual inspection. The minutes to clot formation after CaCl$_2$ addition were measured.

| Temperature for clotting (Timing of tPA Addition) | Minutes to Clot Formation (After CaCl$_2$ Addition) | | | |
|---|---|---|---|---|
| | Control (0.1% HSA-TBS) | rBPI$_{21}$ ~1 µg/mL | rBPI$_{21}$ ~5 µg/mL | rBPI$_{21}$ ~25 µg/mL |
| R.T. (Pre-clot tPA) | 7 | 7 | 8 | 10 |
| 37° C. (Pre-clot tPA) | 5 | 5 | 6 | 8 |
| 37° C. (Post-clot tPA) | 5 | 5 | 6 | 7 |

Clot formation proceeded more rapidly at 37° C. than at R.T. However, 25 µg/mL rBPI$_{21}$ delayed clot formation at both temperatures. Under the conditions tested in this experiment, the lower concentrations of rBPI$_{21}$ did not appear to have an effect on rate of clot formation.

For the clot dissolution part of this experiment, 15 minutes after CaCl$_2$ addition, 44 µL of tPA (600 units/mL, or 1 µg/mL) were added to post-clot tubes to provide a final concentration of 60 units/mL (or 100 ng/mL). The tubes were placed in a 37° C. water bath and checked for clot dissolution/lysis by visual inspection. Time to clot dissolution in hours (for post-clot addition of tPA) or in minutes (for pre-clot addition of tPA) was measured.

| Temperature for clotting (Timing of tPA Addition) | Minutes/Hours to Clot Lysis (After Placement in Water Bath) | | | |
|---|---|---|---|---|
| | Control (0.1% HSA-TBS) | rBPI$_{21}$ ~1 µg/mL | rBPI$_{21}$ ~5 µg/mL | rBPI$_{21}$ ~25 µg/mL |
| R.T. (Pre-clot tPA) | 38 min. | 33 min. | 37 min. | 38 min. |
| 37° C. (Pre-clot tPA) | 45 min. | 30 min. | 31 min. | 29 min. |
| 37° C. (Post-clot tPA) | 10–12 hours[#] | 7–8 hours[#] | 7–8 hours[#] | 6 hours[#] |

[#]—Time estimated based on clot size at the 7 hour time point.

Clot lysis was greatly accelerated when tPA was added pre-clot formation compared to post-clot formation. For pre-clot tPA addition, rBPI$_{21}$ provided a greater acceleration of clot lysis time when the clot was formed at 37° C. compared to at R.T. (~35% versus ~3%). Al subsequent experiments were performed at 37° C.

G. Effect of rBPI$_{21}$, rBPI$_{50}$, and rLBP

Clot formation and lysis were evaluated with rBPI$_{21}$, rBPI$_{50}$, and rLBP. The following reagents were mixed together in a polypropylene test tube in the following order: (1) 60 μL of 0.1% HSA-TBS; (2) 100 μL of PPP (Donor PC); (3) 40 μL of rBPI$_{21}$, rBPI$_{50}$, or rLBP (either 10, 50 or 250 μg/mL) or buffer control; and (4) 200 μL of 20 mM CaCl$_2$ in TBS, pH 7.8.

The tubes were incubated in a 37° C. water bath and were checked every 1 minute for gel clot formation by visual inspection. The minutes to clot formation after CaCl$_2$ addition were measured.

| | Minutes to Clot Formation (After CaCl$_2$ Addition) | | | |
|---|---|---|---|---|
| Tested Protein | Control (0.1% HSA-TBS) | 1 μg/mL of tested protein | 5 μg/mL of tested protein | 25 μg/mL of tested protein |
| rBPI$_{21}$ | 6 | 5 | 7 | 8 |
| rBPI$_{50}$ | 6 | 4 | 6 | 6 |
| rLBP | 6 | 5 | 5 | 5 |

25 μg/mL rBPI$_{21}$ slowed the rate of clot formation, while rBPI$_{50}$ and rLBP clotting times were comparable to the controls.

For the clot dissolution part of this experiment, 15 minutes after CaCl$_2$ addition, 44 μL of tPA (600 units/mL, 1 μg/mL) were added to all tubes to provide a final concentration of 60 units/mL (100 ng/mL). Then tubes were placed in a 37° C. water bath and checked for clot dissolution/lysis by visual inspection. The minutes to clot dissolution were measured.

| | Hours to Clot Lysis (After Placement in Water Bath) | | | |
|---|---|---|---|---|
| Tested Protein Added | Control (0.1% HSA-TBS) | 1 μg/mL of tested protein | 5 μg/mL of tested protein | 25 μg/mL of tested protein |
| rBPI$_{21}$ | 13–14* | 7 | 7 | 7 |
| rBPI$_{50}$ | 13–14* | 10 | 11 | 7 |
| rLBP | 13–14* | 13–14* | 8 | 11 |

*—Time estimated based on clot size at 11 hours.

At all concentrations tested, rBPI$_{21}$ decreased clot lysis time by approximately 50%. rBPI$_{50}$ decreased clot lysis by approximately 29% at 1 μg/mL, 19% at 5 μg/mL and 50% at 25 μg/mL. rLBP decreased clot lysis time by approximately 57% at 5 μg/mL, approximately 29% at 25 μg/mL, and had no discernable effect at 1 μg/mL. These results show that, on a mass basis, rBPI$_2$ was more potent than rBPI$_{50}$ and rLBP in enhancing the effects of tPA clot dissolution.

H. Effect of Fresh Platelet Rich Plasma (PRP) and Platelet Poor Plasma (PPP)

Clot formation and lysis were evaluated in the presence and absence of rBPI$_{21}$ with freshly collected platelet rich plasma (PRP) and platelet door plasma (PPP) from the same donor. The following reagents were mixed together in a polypropylene test tube in the following order: (1) 120 μL of fresh PRP or PPP (Donor EL); (2) 80 μL of rBPI$_{21}$ (either 5, 25 or 125 μg/mL) or control (0.1% HSA-TBS) and tPA (300 units/mL); and (3) 200 μL of 20 mM CaCl$_2$ in TBS, pH 7.8.

The tubes were incubated in a 37° C. water bath, and were checked every 1 minute for gel clot formation by visual inspection. The minutes to clot formation after CaCl$_2$ addition were measured.

| | Minutes to Clot Formation (After CaCl$_2$ Addition) | | | |
|---|---|---|---|---|
| Type of Plasma | Control (0.1% HSA-TBS) | rBPI$_{21}$ 1 μg/mL | rBPI$_{21}$ 5 μg/mL | rBPI$_{21}$ 25 μg/mL |
| Platelet Poor | 21 | 24 | 36 | 55 |
| Platelet Rich | 15 | 16 | 21 | 37 |

A direct rBPI$_{21}$ dose-response effect on rate of clot formation was observed for both PPP and PRP; higher concentrations of rBPI$_{21}$ produced greater prolongation of clot formation. For all conditions tested in this experiment, PRP exhibited faster clotting times than PPP.

For the clot dissolution part of this experiment, incubation was continued at 37° C. without further addition of reagents. The minutes to clot dissolution were measured.

| | Minutes to Clot Lysis (After CaCl$_2$ Addition) | | | |
|---|---|---|---|---|
| Type of Plasma | Control (0.1% HSA-TBS) | rBPI$_{21}$ 1 μg/mL | rBPI$_{21}$ 5 μg/mL | rBPI$_{21}$ 25 μg/mL |
| Platelet Poor | 71 | 59 | 66 | 86 |
| Platelet Rich | 81 | 65 | 66 | 81 |

For all conditions tested, the fresh PRP had longer clot dissolution times than fresh PPP. For each plasma type (PRP or PPP), clot dissolution was fastest at the 1 μg/mL concentration of rBPI$_{21}$. The time from clot formation to clot dissolution is calculated and shown below.

| | Duration of Clot (Time of Clot Formation Subtracted From Time of Clot Lysis) | | | |
|---|---|---|---|---|
| Type of Plasma | Control (0.1% HSA-TBS) | rBPI$_{21}$ 1 μg/mL | rBPI$_{21}$ 5 μg/mL | rBPI$_{21}$ 25 μg/mL |
| Platelet Poor | 50 | 35 | 30 | 31 |
| Platelet Rich | 66 | 49 | 45 | 44 |

In this experiment, a dose response effect was observed for clot formation; increasing rBPI$_{21}$ concentration resulted in increasing clotting times in both PRP and PPP. However, a rBPI$_{21}$ dose response effect was not clearly observed for clot dissolution. Overall, faster clot dissolution times were observed for rBPI$_{21}$ at 1 μg/mL. However, if the time between clot formation to clot dissolution is measured, then there are only modest differences in clot dissolution times. From these results, it appeared that at lower rBPI$_{21}$ concentrations, greater effects were observed on clot dissolution rather than clot formation. As rBPI$_{21}$ concentration was increased, greater effects were observed on clot formation rather than clot dissolution.

I. Effect of rBPI$_{21}$ on Freshly Collected Blood

Clot formation was evaluated with rBPI$_{21}$ and freshly collected blood. For this experiment, blood was collected into four siliconized 3 mL Vacutainer® tubes containing either 50, 100, 200 μg/ml rBPI$_{21}$ or control formulation buffer. Each tube was inverted several times after blood collection and placed on ice until blood had been collected for all tubes. (Collection time of each tube was less than thirty seconds.)

All tubes were placed in a 37° C. water bath and checked every one minute by gently tipping the tube and visually inspecting it for clot formation.

| Type of Plasma | Minutes to Clot Formation (After Placement in 37° C. Water Bath) | | | |
|---|---|---|---|---|
| | Control (0.1% HSA-TBS) | rBPI$_{21}$ 50 μg/mL | rBPI$_{21}$ 100 μg/mL | rBPI$_{21}$ 200 μg/mL |
| Whole Blood (Donor PM) | 6 | 11 | 16 | 30 |

Increasing rBPI$_{21}$ concentration slowed the rate of clot formation in a dose dependent manner, but did not completely prevent clot formation.

EXAMPLE 2

EFFECTS OF BPI PROTEIN PRODUCTS ON CLOT FORMATION AND CLOT LYSIS IN MICROTITER PLATE ASSAYS

A 96-well microtiter plate assay was used to evaluate the effects of a BPI protein product on clot formation under a variety of conditions using human plasma samples. These assays confirmed the results of tube assays described in Example 1. For these assays, human plasma, either PRP or PPP, was prepared as described in Example 1.

For the plate-based assay, all experiments were conducted at 37° C. and total volume per well was ~200 μL in the presence or absence of tPA as a pre-clot addition or ~250 μL where tPA (50 μL) was added post-clot formation to the 200 μL containing well.

A. Effect of BPI Protein Product and Pre-Clot Addition of tPA: Fresh PRP and PPP Clot formation was evaluated when rBPI$_{21}$ and tPA were added to fresh PRP or PPP prior to calcium addition. The following reagents were added to each well of a 96 well microtiter plate (e.g., Dynatec, Chantilly, Va., CoStar, Cambridge, Mass.) in the following order: (1) 60 μL of 0.1% HSA-TBS; (2) 50 μL of fresh PRP or PPP (Donor PM); (3) 20 μL of rBPI$_{21}$ (1000, 250, 50, 10 or 2 μg/mL); (4) 20 μL of tPA (600 units/mL, 100 ng/mL); and (5) 50 μL of 20 mM CaCl$_2$ in TBS, pH 7.4.

Immediately after CaCl$_2$ addition, the turbidity of the wells was measured as the optical density at 405 nm at various times (in this experiment at 2 minute intervals for 2 hours) by using an automatic plate reader (Vmax Plate Reader, Molecular Devices, Menlo Park, Calif.). The entire plate was scanned within 5 seconds. The OD$_{405}$ versus time data at 2 minute intervals over a 2 hour period was plotted. The rate of clot formation was measured as a change in OD$_{405}$ over time, i.e., as the clot formed the OD$_{405}$ increased. After the peak OD$_{405}$ was achieved, the pre-clot addition of tPA allowed dissolution of the clot as measured by a decrease in OD$_{405}$ over time.

In this experiment, rBPI$_{21}$ completely prevented clot formation of both PRP and PPP at concentrations of 5, 25 and 100 μg/ml. At 1 μg/mL, rBPI$_{21}$ effectively delayed time to clot as measured by a delay in time to peak OD$_{405}$ levels [clot time] and a decrease in peak OD$_{405}$ intensity [clot density]. At 0.2 μg/mL, rBPI$_{21}$ clot formation time was comparable to the control.

B. Effect of Various BPI Protein Products and Control Protein with Pre-Clot Addition of tPA: Frozen PPP Clot formation was evaluated when rBPI$_{21}$, rBPI$_{50}$, rBPI$_{42}$, LBP and thaumatin (a control cationic protein having a similar size and charge as rBPI$_{21}$) and tPA were added to PPP prior to calcium addition. The following reagents were added to each well of a 96 well microtiter plate in the following order: (1) 60 μL of 0.1% HSA-TBS; (2) 50 μL of PPP that had been frozen at −70° C. (Donor PM); (3) 20 μL of protein product (rBPI$_{21}$, rBPI$_{50}$, rBPI$_{42}$, LBP and thaumatin each at 1000, 250, 50, 10 or 2 μg/mL); (4) 20 μL of tPA (600 units/mL, 100 ng/mL); and (5) 50 μL of 20 mM CaCl$_2$ in TBS, pH 7.4.

Immediately after CaCl$_2$ addition, the turbidity of the wells was measured as the OD$_{405}$ at various times as described in part A above. In this experiment, the time to clot formation was determined as the minutes to clot formation as measured by the time at which the OD$_{405}$ had reached its peak value.

| Protein Product | Control | Minutes to Clot Formation | | | | |
|---|---|---|---|---|---|---|
| | | 0.2 μg/mL | 1.0 μg/mL | 5.0 μg/mL | 25.0 μg/mL | 100.0 μg/mL |
| rBPI$_{21}$ | 34 | 32 | 34 | 50 | 50† | No clot |
| rBPI$_{50}$ | 34 | 34 | 34 | 40 | 46† | No clot |
| rBPI$_{42}$ | 40* | 28 | 24 | 20 | 30† | No clot |
| LBP | 34 | 30 | 30 | 32 | 34 | 38 |
| Thaumatin | 40* | 32 | 34 | 32 | 34 | 34 |

†peak height substantially decreased (e.g., 3–4 fold) from control
*higher effective concentration of citrate in formulation buffer control At 100 μg/mL, rBPI$_{21}$, rBPI$_{50}$, rBPI$_{42}$ completely prevented clot formation (as measured by no detectable increase in OD$_{405}$ over the 2 hour kinetic plate reader analysis), and at 25 μg/mL, these BPI protein products substantially prevented clotting (as measured by a slight OD$_{405}$ increase over the 2 hours). At 5 μg/mL, rBPI$_{21}$ and rBPI$_{50}$ effectively delayed time to clot as measured by a delay in time to peak OD$_{405}$ levels. LBP and thaumatin did not affect time to clot formation in this experiment. The lack of effect by the cationic control protein thaumatin indicated that the delay to clot formation by BPI protein products was not simply a charge effect due to their cationic properties.

C. Effect of BPI Protein Product and Pre-Clot Addition of Various Plasminogen Activators: Frozen PPP Clot formation was evaluated when rBPI$_{21}$ and a plasminogen activator (tPA, urokinase or streptokinase) were added to PPP prior to calcium addition. The following reagents were added to each well of a 96 well microtiter plate in the following order: (1) 60 μL of 0.1% HSA-TBS; (2) 50 μL of PPP that had been frozen at −70° C. (Donor PM); (3) 20 μL of rBPI$_{21}$ (1000, 250, 50, 10 or 2 μg/mL); (4) 20 μL of PA (tPA, 1000 ng/mL; for urokinase, 100 and 1000 ng/mL; for streptokinase, 100 and 1000 ng/mL); and (5) 50 μL of 20 mM CaCl$_2$ in TBS, pH 7.4.

Immediately after CaCl$_2$ addition, the turbidity of the wells was measured as the OD$_{405}$ as described in part A above. In this experiment, rBPI$_{21}$ at 100 μg/mL completely prevented clot formation (as measured by no detectable increase in OD$_{405}$ over the 2 hour kinetic plate reader analysis), and at 25 μg/mL, it substantially prevented clotting under conditions where tPA, urokinase or streptokinase was present in the pre-clot mixture. Effects on decreasing clot formation were observed with 5 μg/mL rBPI$_{21}$. At 1 and 0.2 μg/mL, rBPI$_{21}$ clot formation time was comparable to the control. At the concentrations of urokinase tested (10 and 100 ng/mL), clot dissolution did not occur following clot formation, as it did with 100 ng/mL tPA and 100 ng/mL (but not 10 ng/mL) streptokinase.

D. Effect of BPI Protein Product on Plasma from Various Donors: Fresh PPP

Clot formation was evaluated when $rBPI_{21}$ (but not tPA) was added to fresh PPP prior to calcium addition. The following reagents were added to each well of a 96 well microtiter plate in the following order: (1) 80 μL of 0.1% HSA-TBS; (2) 50 μL of fresh PPP (Donors MW, RD and RL); (3) 20 μL of $rBPI_{21}$ (1000, 250, 50, 10 or 2 μg/mL); and (4) 50 μL of 20 mM $CaCl_2$ in TBS, pH 7.4.

Immediately after $CaCl_2$ addition, the turbidity of the wells was measured as the $OD_{405}$ as described in part A above. In this experiment, $rBPI_{21}$ at various concentrations slowed or prevented clot formation. Some individual variation was observed in the response among the three donor plasma samples simultaneously tested. For all three donors, $rBPI_{21}$ at 25 and 100 μg/mL completely prevented clot formation of fresh PPP. At 5 μg/mL, $rBPI_{21}$ also completely prevented clot formation of the PPP from one donor (RL) and substantially prevented clotting of the PPP from the other two donors (MW and RD). At 1 μg/mL, $rBPI_{21}$ substantially prevented clotting of the PPP from one donor (RL), and reduced clotting was observed in the PPP of the other two donors (MW and RD). A slight effect was observed even at 0.2 μg/mL $rBPI_{21}$ with one donor; generally at 0.2 μg/mL $rBPI_{21}$, clot formation was comparable to control.

E. Effect of Multiple BPI Protein Products After Thrombin-Driven Clot Formation and Post-Clot tPA Addition: Fresh PPP Clot lysis was evaluated when $rBPI_{21}$ and tPA were added to fresh PPP with 0.125 units/mL thrombin and calcium. The following reagents were added to each well of a 96 well microtiter plate in the following order: (1) 80 μL of 0.1% HSA-TBS; (2) 50 μL of PPP that had been frozen at −70° C. (Donor PM); (3) 20 μL of $rBPI_{21}$ or $rBPI_{42}$ (50, 10 or 2 μg/mL); and (4) 50 μL of 20 mM $CaCl_2$ in TBS, pH 7.4 with 0.5 units/mL thrombin.

After thrombin and $CaCl_2$ addition, clot formation was allowed to occur and 50 μL of tPA (300 units/mL, 500 ng/mL) with 0.5 units/mL of heparin in TBS, pH 7.4 were added. After clot formation and tPA addition (~15 minutes), the turbidity of the wells was measured as the $OD_{405}$. In this initial experiment with thrombin-driven clot formation, $rBPI_{21}$ or $rBPI_{42}$ with post-clot addition of tPA allowed dissolution of the clot as measured by a decrease in $OD_{405}$ over time. Increasing the concentration of $rBPI_{21}$ or $rBPI_{42}$ (0.2, 1 and 5 μg/mL) with a constant concentration of tPA (100 ng/mL) resulted in enhanced clot dissolution (i.e., the rate at which the $OD_{405}$ decreased was ~2–4 fold faster).

EXAMPLE 3

EFFECTS OF BPI PROTEIN PRODUCT ON tPA-INDUCED CLOT LYSIS IN A RAT THROMBOSIS MODEL

A rat thrombosis model was used to determine the effects of a BPI protein product ($rBPI_{21}$) with a thrombolytic agent (tPA) on clot lysis and reocclusion after thrombolytic therapy. The methods of Klement et al., *Thrombosis Haemostasis*, 68:64–68 (1992), were modified as described herein to determine the effects of $rBPI_{21}$ in 5 mM citrate, 150 mM NaCl, 0.2% poloxamer 188, 0.002% polysorbate 80 on tPA-induced clot lysis in vivo. In this experiment, two groups of rats (5 for the vehicle-treated group and 5 for the $rBPI_{21}$-treated group) were anesthetized with ketamine/Rompum, and catheters were placed in both jugular veins for administration of therapeutic agents. The right common carotid artery was cannulated to measure blood pressure and heart rate. A midline incision was made in the lower abdomen to expose the terminal aorta and iliac vessels, which were dissected free of connective tissue and separated from the vena cava, where possible, and the great veins. All of the numerous small branches from the aorta that were observed were ligated in order to isolate a section of the vessel approximately 1 cm in length. The left iliac artery was cannulated with a 20 gauge blunt needle sealed with a rubber septum. An ultrasonic flow transducer cuff was placed around the right iliac artery in order to measure blood flow with a flow meter [Crystal Biotech, Holliston, Mass.]. The flow signal was recorded on a chart recorder.

The following procedures were carried out in order to injure the aorta and thus provide a surface for clot formation. The 20 gauge needle was advanced into the aorta and slowly moved against the vessel wall along a 1 to 1.5 cm length. This was repeated 8 times. The needle was removed and the same area of the aorta was pinched 4 times with smooth forceps. Subsequently, an area of stenosis was produced in the terminal aorta by gently tightening silk thread at two locations. Right iliac blood flow was measured at this time and designated as the "pre-occlusion" level.

At this point, the $rBPI_{21}$-treated rats were administered 20 mg/kg $rBPI_{21}$ as a 2 mg/mL solution in 5 mM citrate 0.2% poloxamer 188, 150 mM NaCl (Pluronic F-68, BASF Wyandotte, Parsippany, N.J.) and 0.002% polysorbate 80 (Tween 80, ICI Americas Inc., Wilmington, Del.), pH 5 as a bolus over 30 seconds (4 mL/kg) intravenously into one of the jugular veins, followed by a constant infusion of $rBPI_{21}$ at 20 mg/kg/hr that was continued until the end of the experiment. The vehicle-treated rats received the same volumes; the vehicle solution was 5 mM citrate 150 mM NaCl, 0.2% poloxamer 188, (Pluronic F-68, BASF Wyandotte, Parsippany, N.J.) and 0.002% polysorbate 80 (Tween 80, ICI Americas Inc., Wilmington, Del.), pH 5. Next, the right iliac artery was occluded with a small metal clip placed just above the blood flow cuff. Since the left iliac artery was already sealed by the needle catheter, blood was then trapped above the occlusion. Finally, the aorta was occluded above the injured site, producing a stenotic area with stasis. The occlusions were maintained for 30 minutes and then removed. Confirmation that a clot had formed was provided by the failure to record flow through the right iliac artery.

Five minutes after removal of the occlusions, t-PA was administered into the other jugular vein (in which $rBPI_{21}$ had not been administered) as a bolus of 1 mg/kg followed by an infusion of 1 mg/kg over 1 hour. After 1 hour, both the tPA and the $rBPI_{21}$ (or vehicle) infusions were discontinued and the experiment was terminated. Clot lysis was defined as a return of blood flow through the right iliac artery to 50% of the pre-occlusion level. The length of time until clot lysis was recorded, as well as the time until the first reocclusion after the initial clot lysis. The number of times that the vessel became reoccluded over the 1 hour period of t-PA treatment was also recorded. Reocclusion was defined as a reduction in blood flow to 10% of the pre-occlusion level. Statistical comparisons between the buffer- and $rBPI_{21}$-treated groups were done with Student's T test. Neither t-PA nor $rBPI_{21}$ produced any adverse systemic effects, other than a rise in blood pressure due solely to the aortic occlusion.

The results revealed no significant difference in the mean time to clot lysis, which was 14.4±5.1 minutes for the buffer-treated group and 16.1±4.2 minutes for the $rBPI_{21}$-treated group. Multiple reocclusion episodes occurred in all rats. The time to the first reocclusion was not significantly different between the two groups. However, the number of reocclusions was statistically significantly reduced in rBPI$_{21}$-treated rats (p<0.05); the rBPI$_{21}$-treated rats averaged 4±1.6 reocclusion episodes, while the buffer-treated rats averaged 9±1.7 reocclusion episodes.

Numerous modifications and variations of the above-described invention are expected to occur to those of skill in the art. Accordingly, only such limitations as appear in the appended claims should be placed thereon.

---

What is claimed is:

1. A method for slowing clot formation in blood comprising administering to a subject suffering from a thrombotic disorder a bactericidal/permeability-increasing protein (BPI) protein product in an amount effective to delay or prevent clot formation in the blood.

2. A method for enhancing clot dissolution in blood comprising administering to a subject suffering from a thrombotic disorder a BPI protein product in an amount effective to enhance clot dissolution in the blood.

3. The method of claim 1 or 2 wherein the BPI protein product is an amino-terminal fragment of BPI protein having a molecular weight of about 21 kD to 25 kD.

4. The method of claim 1 or 2 wherein the BPI protein product is $rBPI_{23}$ or a dimeric form thereof.

5. The method of claim 1 or 2 wherein the BPI protein product is $rBPI_{21}$.

6. The method of claim 1 or 2 wherein the subject is concurrently administered another antithrombotic agent.

* * * * *

UNITED STATES PATENT AND TRADEMARK OFFICE
CERTIFICATE OF CORRECTION

PATENT NO.    : 6,107,280
DATED         : August 22, 2000
INVENTOR(S)   : White et al.

It is certified that error appears in the above-identified patent and that said Letters Patent is hereby corrected as shown below:

At Col. 34, line 40, in claim 3, "terninal" should be --terminal--.

Signed and Sealed this

Tenth Day of April, 2001

Attest:

NICHOLAS P. GODICI

Attesting Officer   Acting Director of the United States Patent and Trademark Office

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1813 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 31..1491

(ix) FEATURE:
      (A) NAME/KEY: mat_peptide
      (B) LOCATION: 124..1491

(ix) FEATURE:
      (A) NAME/KEY: misc_feature
      (D) OTHER INFORMATION: "rBPI"

(xi) SEQUENCE DESCRIPTION: SEQ ID NO:1:

```
CAGGCCTTGA GGTTTTGGCA GCTCTGGAGG ATG AGA GAG AAC ATG GCC AGG GGC        54
                                Met Arg Glu Asn Met Ala Arg Gly
                                -31 -30                     -25

CCT TGC AAC GCG CCG AGA TGG GTG TCC CTG ATG GTG CTC GTC GCC ATA        102
Pro Cys Asn Ala Pro Arg Trp Val Ser Leu Met Val Leu Val Ala Ile
            -20             -15                 -10

GGC ACC GCC GTG ACA GCG GCC GTC AAC CCT GGC GTC GTG GTC AGG ATC        150
Gly Thr Ala Val Thr Ala Ala Val Asn Pro Gly Val Val Val Arg Ile
        -5              1               5

TCC CAG AAG GGC CTG GAC TAC GCC AGC CAG CAG GGG ACG GCC GCT CTG        198
Ser Gln Lys Gly Leu Asp Tyr Ala Ser Gln Gln Gly Thr Ala Ala Leu
 10              15              20                      25

CAG AAG GAG CTG AAG AGG ATC AAG ATT CCT GAC TAC TCA GAC AGC TTT        246
Gln Lys Glu Leu Lys Arg Ile Lys Ile Pro Asp Tyr Ser Asp Ser Phe
                    30              35                  40

AAG ATC AAG CAT CTT GGG AAG GGG CAT TAT AGC TTC TAC AGC ATG GAC        294
Lys Ile Lys His Leu Gly Lys Gly His Tyr Ser Phe Tyr Ser Met Asp
            45                  50                  55

ATC CGT GAA TTC CAG CTT CCC AGT TCC CAG ATA AGC ATG GTG CCC AAT        342
Ile Arg Glu Phe Gln Leu Pro Ser Ser Gln Ile Ser Met Val Pro Asn
        60              65                  70

GTG GGC CTT AAG TTC TCC ATC AGC AAC GCC AAT ATC AAG ATC AGC GGG        390
Val Gly Leu Lys Phe Ser Ile Ser Asn Ala Asn Ile Lys Ile Ser Gly
    75              80                  85

AAA TGG AAG GCA CAA AAG AGA TTC TTA AAA ATG AGC GGC AAT TTT GAC        438
Lys Trp Lys Ala Gln Lys Arg Phe Leu Lys Met Ser Gly Asn Phe Asp
 90                  95                  100                 105

CTG AGC ATA GAA GGC ATG TCC ATT TCG GCT GAT CTG AAG CTG GGC AGT        486
Leu Ser Ile Glu Gly Met Ser Ile Ser Ala Asp Leu Lys Leu Gly Ser
                    110                 115                 120

AAC CCC ACG TCA GGC AAG CCC ACC ATC ACC TGC TCC AGC TGC AGC AGC        534
```

```
                Asn Pro Thr Ser Gly Lys Pro Thr Ile Thr Cys Ser Ser Cys Ser Ser
                            125                 130                 135

CAC ATC AAC AGT GTC CAC GTG CAC ATC TCA AAG AGC AAA GTC GGG TGG           582
His Ile Asn Ser Val His Val His Ile Ser Lys Ser Lys Val Gly Trp
            140                 145                 150

CTG ATC CAA CTC TTC CAC AAA AAA ATT GAG TCT GCG CTT CGA AAC AAG           630
Leu Ile Gln Leu Phe His Lys Lys Ile Glu Ser Ala Leu Arg Asn Lys
155                 160                 165

ATG AAC AGC CAG GTC TGC GAG AAA GTG ACC AAT TCT GTA TCC TCC AAG           678
Met Asn Ser Gln Val Cys Glu Lys Val Thr Asn Ser Val Ser Ser Lys
170                 175                 180                 185

CTG CAA CCT TAT TTC CAG ACT CTG CCA GTA ATG ACC AAA ATA GAT TCT           726
Leu Gln Pro Tyr Phe Gln Thr Leu Pro Val Met Thr Lys Ile Asp Ser
                190                 195                 200

GTG GCT GGA ATC AAC TAT GGT CTG GTG GCA CCT CCA GCA ACC ACG GCT           774
Val Ala Gly Ile Asn Tyr Gly Leu Val Ala Pro Pro Ala Thr Thr Ala
            205                 210                 215

GAG ACC CTG GAT GTA CAG ATG AAG GGG GAG TTT TAC AGT GAG AAC CAC           822
Glu Thr Leu Asp Val Gln Met Lys Gly Glu Phe Tyr Ser Glu Asn His
            220                 225                 230

CAC AAT CCA CCT CCC TTT GCT CCA CCA GTG ATG GAG TTT CCC GCT GCC           870
His Asn Pro Pro Pro Phe Ala Pro Pro Val Met Glu Phe Pro Ala Ala
        235                 240                 245

CAT GAC CGC ATG GTA TAC CTG GGC CTC TCA GAC TAC TTC TTC AAC ACA           918
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA           966
Ala Gly Leu Val Tyr Gln Glu Ala Gly Val Leu Lys Met Thr Leu Arg
                270                 275                 280

GAT GAC ATG ATT CCA AAG GAG TCC AAA TTT CGA CTG ACA ACC AAG TTC          1014
Asp Asp Met Ile Pro Lys Glu Ser Lys Phe Arg Leu Thr Thr Lys Phe
            285                 290                 295

TTT GGA ACC TTC CTA CCT GAG GTG GCC AAG AAG TTT CCC AAC ATG AAG          1062
Phe Gly Thr Phe Leu Pro Glu Val Ala Lys Lys Phe Pro Asn Met Lys
            300                 305                 310

ATA CAG ATC CAT GTC TCA GCC TCC ACC CCG CCA CAC CTG TCT GTG CAG          1110
Ile Gln Ile His Val Ser Ala Ser Thr Pro Pro His Leu Ser Val Gln
        315                 320                 325

CCC ACC GGC CTT ACC TTC TAC CCT GCC GTG GAT GTC CAG GCC TTT GCC          1158
Pro Thr Gly Leu Thr Phe Tyr Pro Ala Val Asp Val Gln Ala Phe Ala
330                 335                 340                 345

GTC CTC CCC AAC TCC TCC CTG GCT TCC CTC TTC CTG ATT GGC ATG CAC          1206
Val Leu Pro Asn Ser Ser Leu Ala Ser Leu Phe Leu Ile Gly Met His
                350                 355                 360

ACA ACT GGT TCC ATG GAG GTC AGC GCC GAG TCC AAC AGG CTT GTT GGA          1254
Thr Thr Gly Ser Met Glu Val Ser Ala Glu Ser Asn Arg Leu Val Gly
            365                 370                 375

GAG CTC AAG CTG GAT AGG CTG CTC CTG GAA CTG AAG CAC TCA AAT ATT          1302
Glu Leu Lys Leu Asp Arg Leu Leu Leu Glu Leu Lys His Ser Asn Ile
            380                 385                 390

GGC CCC TTC CCG GTT GAA TTG CTG CAG GAT ATC ATG AAC TAC ATT GTA          1350
Gly Pro Phe Pro Val Glu Leu Leu Gln Asp Ile Met Asn Tyr Ile Val
        395                 400                 405

CCC ATT CTT GTG CTG CCC AGG GTT AAC GAG AAA CTA CAG AAA GGC TTC          1398
Pro Ile Leu Val Leu Pro Arg Val Asn Glu Lys Leu Gln Lys Gly Phe
410                 415                 420                 425

CCT CTC CCG ACG CCG GCC AGA GTC CAG CTC TAC AAC GTA GTG CTT CAG          1446
Pro Leu Pro Thr Pro Ala Arg Val Gln Leu Tyr Asn Val Val Leu Gln
                430                 435                 440
```

```
CCT CAC CAG AAC TTC CTG CTG TTC GGT GCA GAC GTT GTC TAT AAA              1491
Pro His Gln Asn Phe Leu Leu Phe Gly Ala Asp Val Val Tyr Lys
            445                 450                 455

TGAAGGCACC AGGGGTGCCG GGGGCTGTCA GCCGCACCTG TTCCTGATGG GCTGTGGGGC        1551

ACCGGCTGCC TTTCCCCAGG GAATCCTCTC CAGATCTTAA CCAAGAGCCC CTTGCAAACT        1611

TCTTCGACTC AGATTCAGAA ATGATCTAAA CACGAGGAAA CATTATTCAT TGGAAAAGTG        1671

CATGGTGTGT ATTTTAGGGA TTATGAGCTT CTTTCAAGGG CTAAGGCTGC AGAGATATTT        1731

CCTCCAGGAA TCGTGTTTCA ATTGTAACCA AGAAATTTCC ATTTGTGCTT CATGAAAAAA        1791

AACTTCTGGT TTTTTTCATG TG                                                 1813
```

(2) INFORMATION FOR SEQ ID NO:2:

(i) SEQUENCE CHARACTERISTICS:
        (A) LENGTH: 487 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Glu Asn Met Ala Arg Gly Pro Cys Asn Ala Pro Arg Trp Val
-31 -30                 -25                 -20

Ser Leu Met Val Leu Val Ala Ile Gly Thr Ala Val Thr Ala Ala Val
-15                 -10                  -5                   1

Asn Pro Gly Val Val Val Arg Ile Ser Gln Lys Gly Leu Asp Tyr Ala
                 5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
            35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
            85                  90                  95

Leu Lys Met Ser Gly Asn Phe Asp Leu Ser Ile Glu Gly Met Ser Ile
            100                 105                 110

Ser Ala Asp Leu Lys Leu Gly Ser Asn Pro Thr Ser Gly Lys Pro Thr
            115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
            180                 185                 190

Pro Val Met Thr Lys Ile Asp Ser Val Ala Gly Ile Asn Tyr Gly Leu
            195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240
```

```
Pro Val Met Glu Phe Pro Ala Ala His Asp Arg Met Val Tyr Leu Gly
            245             250             255

Leu Ser Asp Tyr Phe Phe Asn Thr Ala Gly Leu Val Tyr Gln Glu Ala
            260             265             270

Gly Val Leu Lys Met Thr Leu Arg Asp Asp Met Ile Pro Lys Glu Ser
    275             280             285

Lys Phe Arg Leu Thr Thr Lys Phe Phe Gly Thr Phe Leu Pro Glu Val
290             295             300             305

Ala Lys Lys Phe Pro Asn Met Lys Ile Gln Ile His Val Ser Ala Ser
            310             315             320

Thr Pro Pro His Leu Ser Val Gln Pro Thr Gly Leu Thr Phe Tyr Pro
            325             330             335

Ala Val Asp Val Gln Ala Phe Ala Val Leu Pro Asn Ser Ser Leu Ala
            340             345             350

Ser Leu Phe Leu Ile Gly Met His Thr Thr Gly Ser Met Glu Val Ser
    355             360             365

Ala Glu Ser Asn Arg Leu Val Gly Glu Leu Lys Leu Asp Arg Leu Leu
370             375             380             385

Leu Glu Leu Lys His Ser Asn Ile Gly Pro Phe Pro Val Glu Leu Leu
            390             395             400

Gln Asp Ile Met Asn Tyr Ile Val Pro Ile Leu Val Leu Pro Arg Val
            405             410             415

Asn Glu Lys Leu Gln Lys Gly Phe Pro Leu Pro Thr Pro Ala Arg Val
            420             425             430

Gln Leu Tyr Asn Val Val Leu Gln Pro His Gln Asn Phe Leu Leu Phe
    435             440             445

Gly Ala Asp Val Val Tyr Lys
450             455
```